(12) United States Patent
O'Brien et al.

(10) Patent No.: US 8,343,915 B2
(45) Date of Patent: *Jan. 1, 2013

(54) USE OF HEAT-SHOCK PROTEIN 27 FOR CARDIOVASCULAR DISEASE PREVENTION AND TREATMENT

(75) Inventors: Edward R. M. O'Brien, Ottawa (CA); Katey Rayner, Ottawa (CA); Yong-Xiang Chen, Ottawa (CA); Xiaoli Ma, Ottawa (CA)

(73) Assignee: Ottawa Heart Institute Research Corporation, Ottawa (CA)

(*) Notice: Subject to any disclaimer, the term of this patent is extended or adjusted under 35 U.S.C. 154(b) by 409 days.

This patent is subject to a terminal disclaimer.

(21) Appl. No.: 12/228,261

(22) Filed: Aug. 11, 2008

(65) Prior Publication Data

US 2009/0054340 A1 Feb. 26, 2009

Related U.S. Application Data

(60) Provisional application No. 60/955,210, filed on Aug. 10, 2007.

(51) Int. Cl.
*A61K 38/00* (2006.01)
(52) U.S. Cl. ........................................ 514/7.4
(58) Field of Classification Search ................ None
See application file for complete search history.

(56) References Cited

U.S. PATENT DOCUMENTS

2001/0049357 A1* 12/2001 De et al. ............... 514/12

OTHER PUBLICATIONS

Lusis (Atherosclerosis, Nature, Sep. 14, 2000; 407(6801): 233-41).*
Jözefowicz-Okonkwo et al. (Is Hsp27 a marker of myocardial ischaemia, Kardiologia Polska, 2009; 67: 9, pp. 947-952).*
Miller et al., "Modulation of Estrogen by the Novel Interaction of Heat Shock Protein 27, a Biomarker for Atherosclerosis, and Estrogen Receptor Beta: Mechanistic Insight Into the Vascular Effects of Estrogens", www.atvb.ahajournals.org, Jan. 20, 2005, pp. 10-14.
Hulley et al., "Randomized Trial of Estrogen Plus Progestin for Secondary Prevention of Coronary Heart Disease in Postmenopausal Women", www.jama.com, JAMA, vol. 280. No. 7, Aug. 19, 1998, pp. 605-613.
"Risks and Benefits of Estrogen Plus Progestion in Healthy Postmenopausal Women: Principal Results From the Women's Health Initiative Randomized Controlled Trial", www.jama.com, JAMA, vol. 288, No. 3, Jul. 17, 2002, pp. 321-333.
Waters et al., Women's Ischemic Syndrome Evaluation: Current Status and Future Research Directions Report of the National Heart, Lung and Blood Institute Workshop, Oct. 2-4, 2002, Section 4, Lessons From Hormone Replacement Trials, Circulation 2004, Feb. 17, 2004, 109(6), pp. 53-55.
Turgeon et al., "Hormone Therapy: Physiological Complexity Belies Therapeutic Simplicity", Science, vol. 304, May 28, 2004, pp. 1269-1273.
Mendelhson et al., "The Time Has Come to Stop Letting HERS Tale Wag the Dogma", www.circ.ahajournals.org/cgi/content/full/104/19/2256, Circulation, 2001, pp. 2256-2259.
Losel et al., "Nongenomic Steroid Action: Controversies, Questions and Answers", Physiol Rev 83, 2003, pp. 965-1016.
Hall et al., "The Multifaceted Mechanisms of Estradiol and estrogen Receptor Signaling", The Journal of Biological Chemistry, vol. 276, Oct. 5, 2001, pp. 36869-36872.
Mendelhson et al., "The Protective Effects of Estrogen on the Cardiovascular System", www.nejm.org, New England J. Med., vol. 340, No. 23, Jun. 10, 1999, pp. 1801-1811.
Smith et al., "Coregulator Function: A Key to Understanding Tissue Specificity of Selective receptor Modulators", www. edrv. endojournals.org, Endocrine Reviews 25(1), Feb. 2004, pp. 45-71.
Lindner et al., "Increased Expression of Estrogen Receptor-Beta mRNA in Male Blood Vessels After Vascular Injury", www.circres.ahajournals.org, American Heart Association, 1998, pp. 224-229.
Makela et al., "Differentiation between vasculoprotective and uterotrophic effects of ligands with different binding affinities to estrogen alpha and beta", Proc. Natl. Acad. Sci, vol. 96, Jun. 1999, pp. 7077-7082.
Martin-Ventura et al., "Identification by a Differential Proteomic Approach of Heat Shock Protein 27 as a Potential Marker of Atheroscleroses", www.circ.ahajournals.org, Circulation, 2004, pp. 2216-2219.
Park et al., "Expression of Heat Shock Protein 27 in Human Atherosclerotic Plaques and Increased Plasma Level of heat Shock Protein 27 in Patients With Acute Coronary Syndrome", www.circ.ahajournals.org, Aug. 21, 2006, pp. 886-893.
Wagstaff et al., "Protection of Neuronal Cells from Apoptosis by Hsp27 Delivered with a Herpes Simplex Virus-based Vector", The Journal of Biological Chemistry, vol. 274, No. 8, Feb. 19, 1999, pp. 5061-5069.
Concannon et al., "On the role of Hsp27 in regulating apoptosis", Apoptosis, vol. 8, No. 1, 2003, pp. 61-70.
Zourlidou et al., "Hsp27 overexpression in the R6/2 mouse model of Hungtington's disease: chronic neurodegeneration does not induce Hsp27 activation", Human Molecular Genetics, vol. 16, No. 9, May 1, 2007, pp. 1078-1090.
Asea et al., "Novel Signal Transduction Pathway Utilized by Extracellular HSP70", The Journal of Biological Chemistry, vol. 277, No. 17, Apr. 26, 2002, pp. 15028-15034.
Vabulas et al., "HSP70 as Endogenous Stimulus of the Toll/Interleukin-1 Receptor Signal Pathway", The Journal of Biological Chemistry, vol. 277, No. 17, Apr. 26, 2002, pp. 15107-15112.
Vabulas et al., "The Endoplasmic Reticulum-resident Heat Shock Protein Gp96 Activates Dendritic Cells via the Toll-like Receptor 2/4 Pathway", The Journal of Biological Chemistry, vol. 277, No. 23, Jun. 7, 2002, pp. 20847-20853.

(Continued)

*Primary Examiner* — Suzanne M Noakes
*Assistant Examiner* — Jae W Lee
(74) *Attorney, Agent, or Firm* — Kathleen E. Marsman; Borden Ladner Gervais LLP

(57) ABSTRACT

A method of preventing or treating cardiovascular disease is provided. The method comprises administering heat shock protein 27 (HSP27), a co-factor, variant or analogue thereof. The cardiovascular disease can include atherosclerosis. A pharmaceutical composition comprising HSP27 for use in the prevention or treatment of cardiovascular disease is also provided.

10 Claims, 20 Drawing Sheets

OTHER PUBLICATIONS

Vabulas et al., "Endocytosed HSP602 Use Toll-like Receptor 2 (TLR2) and TLR4 to Activate the Toll/Interleukin-1 Receptor Signaling Pathway in Innate Immune Cells", The Journal of Biological Chemistry, vol. 276, No. 33, Aug. 17, 2001, pp. 31332-31339.

Moore et al., "Scavenger Receptors in Atherosclerosis: Beyond Uptake", Arterisocler Thromb Vasc Biol, www.atvb.ahajournals.org, 2006, pp. 1702-1711.

Kunjathoor et al., "Scavenger Receptors Class A-I/II and CD36 Are the Principal Receptors Responsible for the Uptake of Modified Low Density Lipoprotein Leading to Lipid Loading in Macrophages", The Journal of Biological Chemistry, vol. 277, No. 51, Dec. 20, 2002, pp. 49982-49988.

Sharp et al., "Heat Shock protein 27 rescues motor neurons following nerve injury and preserves muscle function", Experimental Neurology, vol. 198, Apr. 2006, pp. 511-518.

Hollander et al., Overexpression of Wild-Type Heat Shock Protein 27 and a Nonphosphorylatable Heat Shock Protein 27 Mutant Protects Against Ischemia/Reperfusion Injury in a Transgenic Mouse Model, www.circ.ahajournals.org, Circulation, 2004, pp. 3544-3552.

Liu et al., "Over-expression of heat shock protein 27 attenuates doxorubicin-induced cardiac dysfunction in mice", European Journal of Heart Failure, vol. 9, May 2, 2007. pp. 762-769.

Akbar et al., "The Neuroprotective Effects of Heat Shock Protein 27 Overexpression in Transgenic Animals against Kainate-induced Seizures and Hippocampal Cell Death", The Journal of Biological Chemistry, vol. 278, No. 22, May 30, 2003, pp. 19956-19965.

Svensson et al., Major role of HSP70 as a paracrine inducer of cytokine production in human oxidized LDL treated macrophages, Atherosclerosis, vol. 185, Mar. 2006, pp. 32-38.

Mambula et al. "Heat Shock Protein 70 Is Secreted from Tumor Cells by a Nonclassical Pathway Involving Lysosomal Endosomes", The Journal of Immunology, Dec. 1, 2006, vol. 177, pp. 7849-7857.

Andrei et al., "Phospholipases C and A2 control lysosome-mediated IL-1beta secretion: Implications for inflammatory processes", PNAS, vol. 101, No. 26, Jun. 29, 2004, pp. 9745-9750.

Binder et al., "The heat-shock protein receptors: some answers and more questions", Tissue Antigens, vol. 64, Oct. 2004, pp. 442-451.

Berwin et al., "Scavenger receptor-A mediates gp96/GRP94 and calreticulin internalization by antigen-presenting cells", The EMBO Journal, vol. 22, No. 22, Nov. 17 2003, pp. 6127-6136.

Redon et al., "Global variation in number in the human genome", vol. 444, No. 23, Nov. 23, 2006, pp. 444-455.

Stranger et al., "Relative Impact of Nucleotide and Number Variation on Gene Expression Phenotypes", vol. 315, Feb. 9, 2007, pp. 848-853.

Wang et al., "Multiplex ligation-dependent probe amplification of LDLR enhances molecular diagnosis of familial hypercholesrerolemia", Journal of Lipid Research, vol. 46, Feb. 2005, pp. 366-372.

Feuk et al., "Structural variation in the human genome", Genetics, vol. 7, Feb. 2006, pp. 85-97.

Hegele et al., "Number variations add a new layer complexity in the human genome", CMAJ, vol. 176, No. 4, Feb. 13, 2007, pp. 441-442.

Freeman et al., "Number variation: New Insights in genome diversity", www.genome.cshlp.org, Genome Research. vol. 16, Aug. 2006, pp. 949-961.

Feuk et al., "Structural variants: changing the landscape of chromosomes and design of disease studies", Human Molecular Genetics, vol. 15, No. 1, Apr. 15, 2006, pp. 57-66.

Chen et al., "Screening of number polymorphisms in human Beta-defensin genes using modified real-time quantitative PCR", Journal of Immunological Methods, vol. 308, Jan. 20, 2006, pp. 231-240.

Rayner et al., "Extracellular Release of the Atheroprotective Heat Shock Protein 27 Is Mediated by Estrogen and Competitively Inhibits acLDL Binding to Scavenger Receptor-A", Circulation Research, vol. 103, Jun. 19, 2008, pp. 133-141.

\* cited by examiner

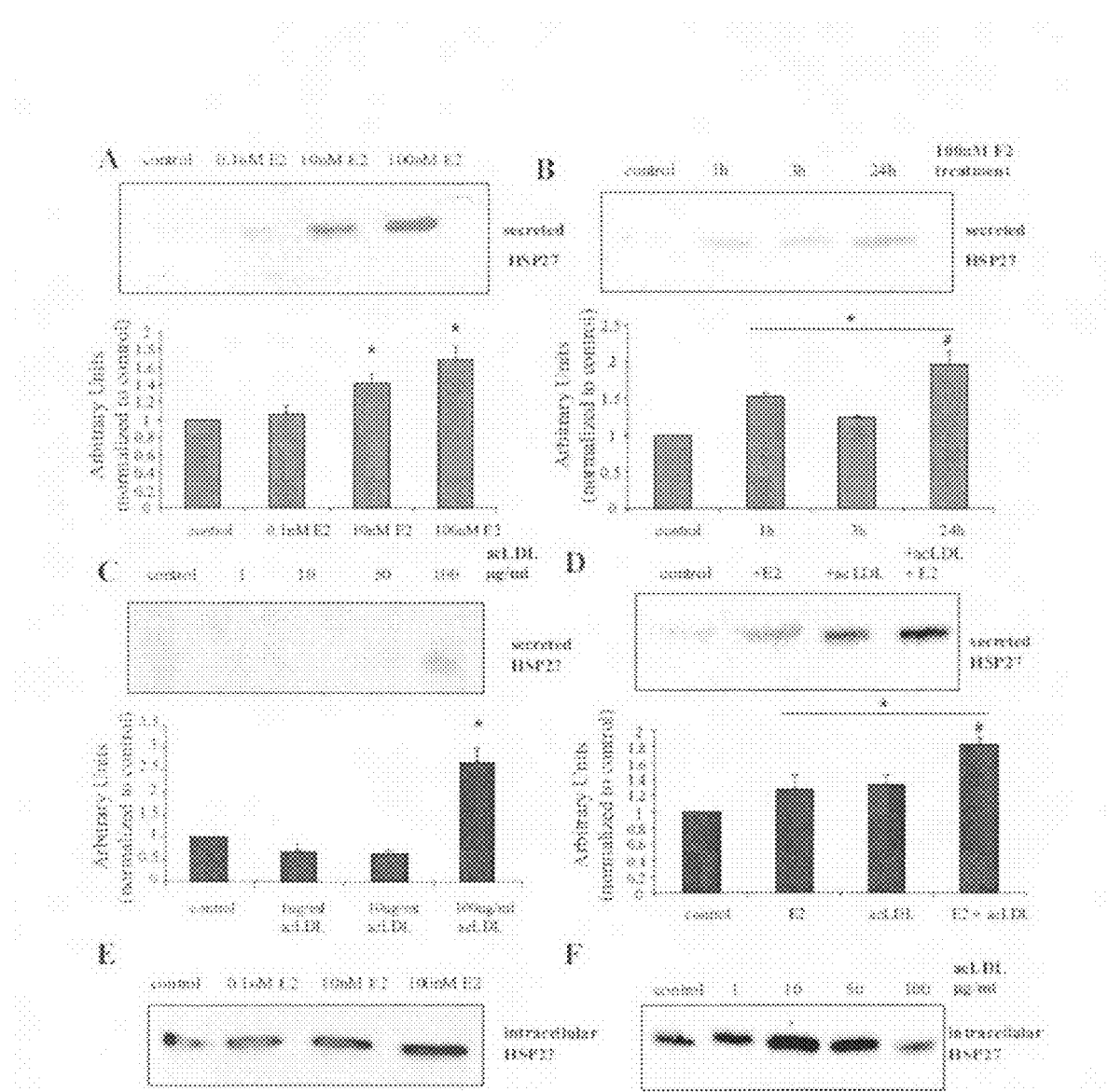
Figure 4 (A-F)

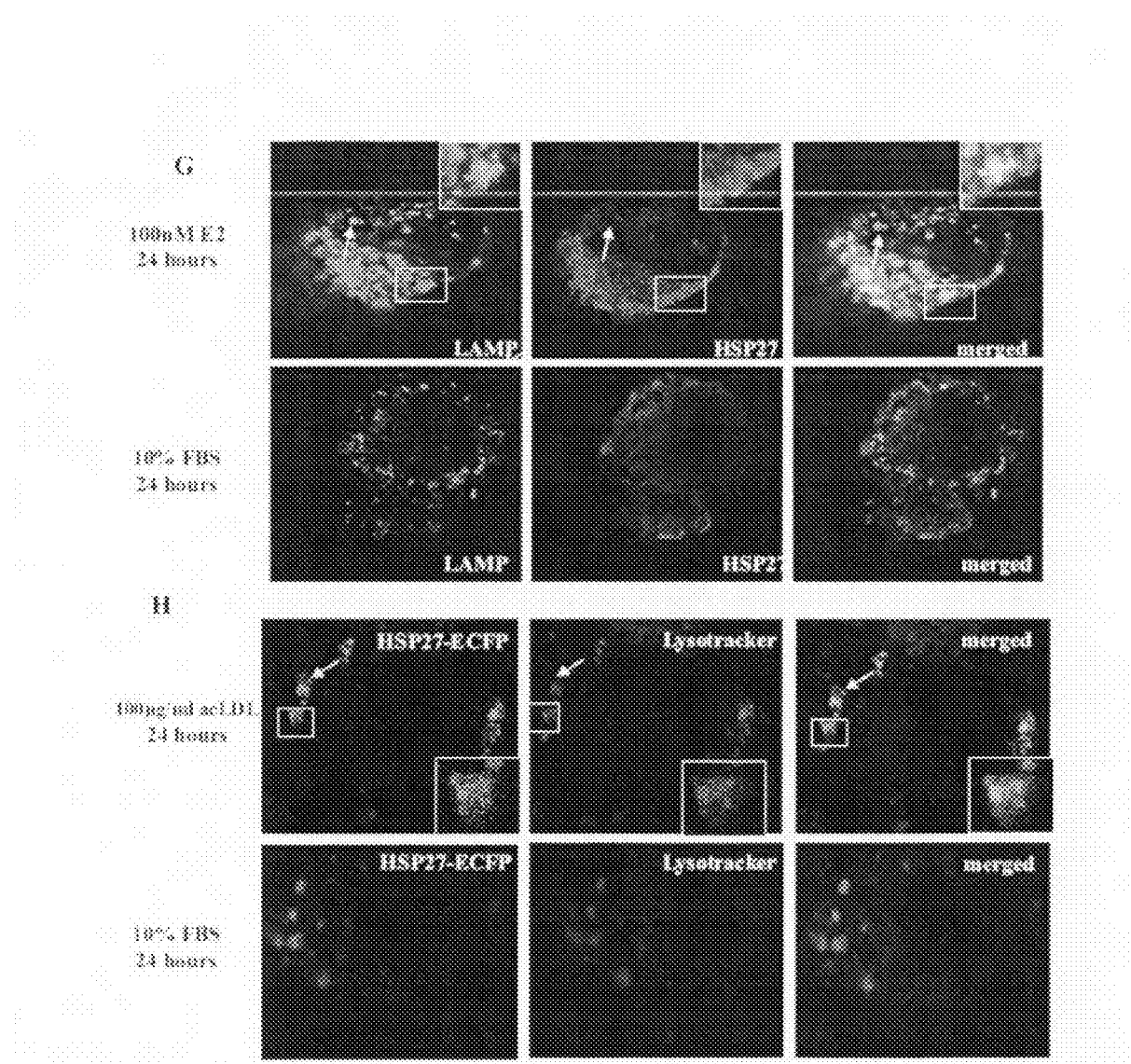
Figure 4 (G-H)

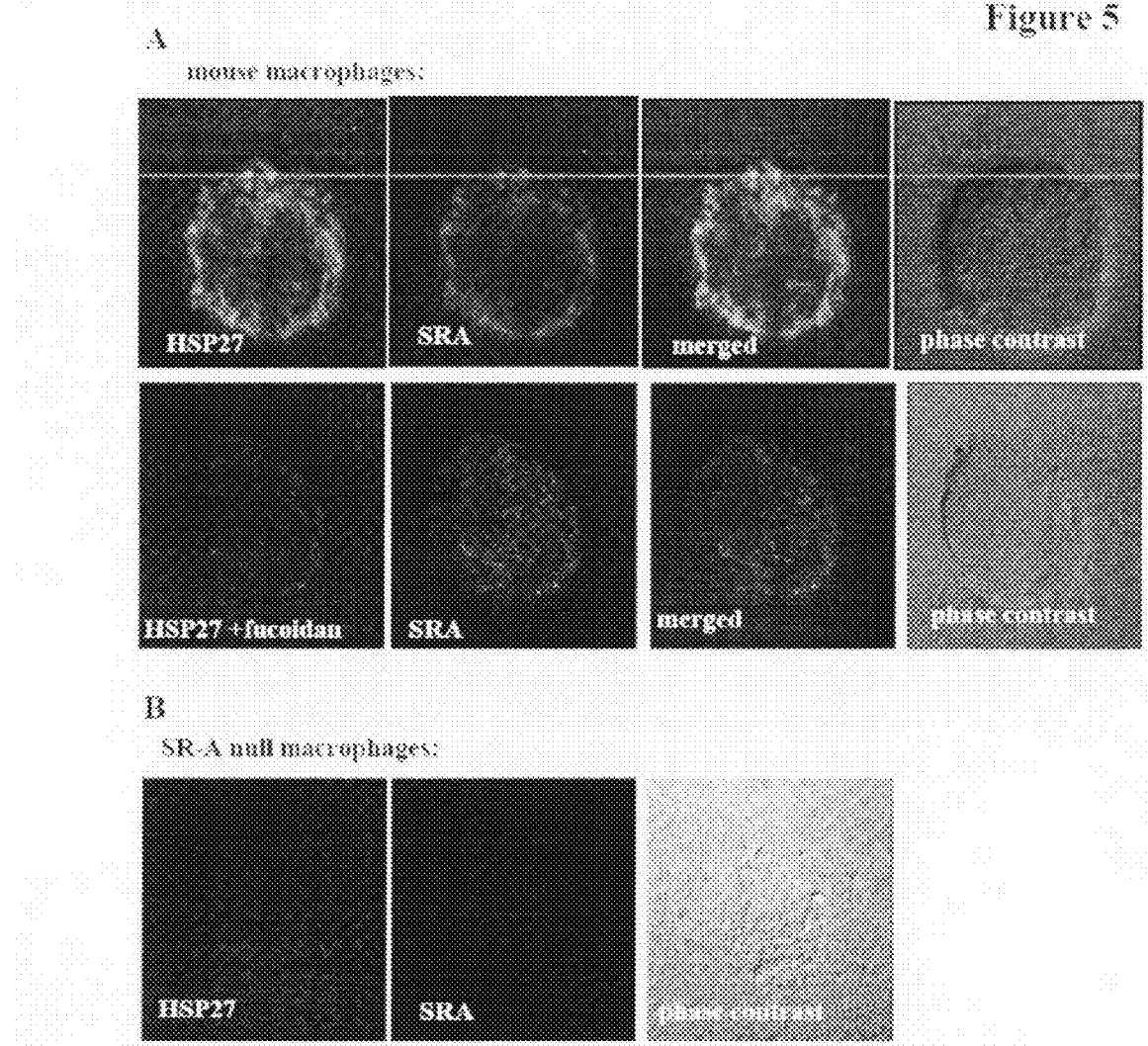

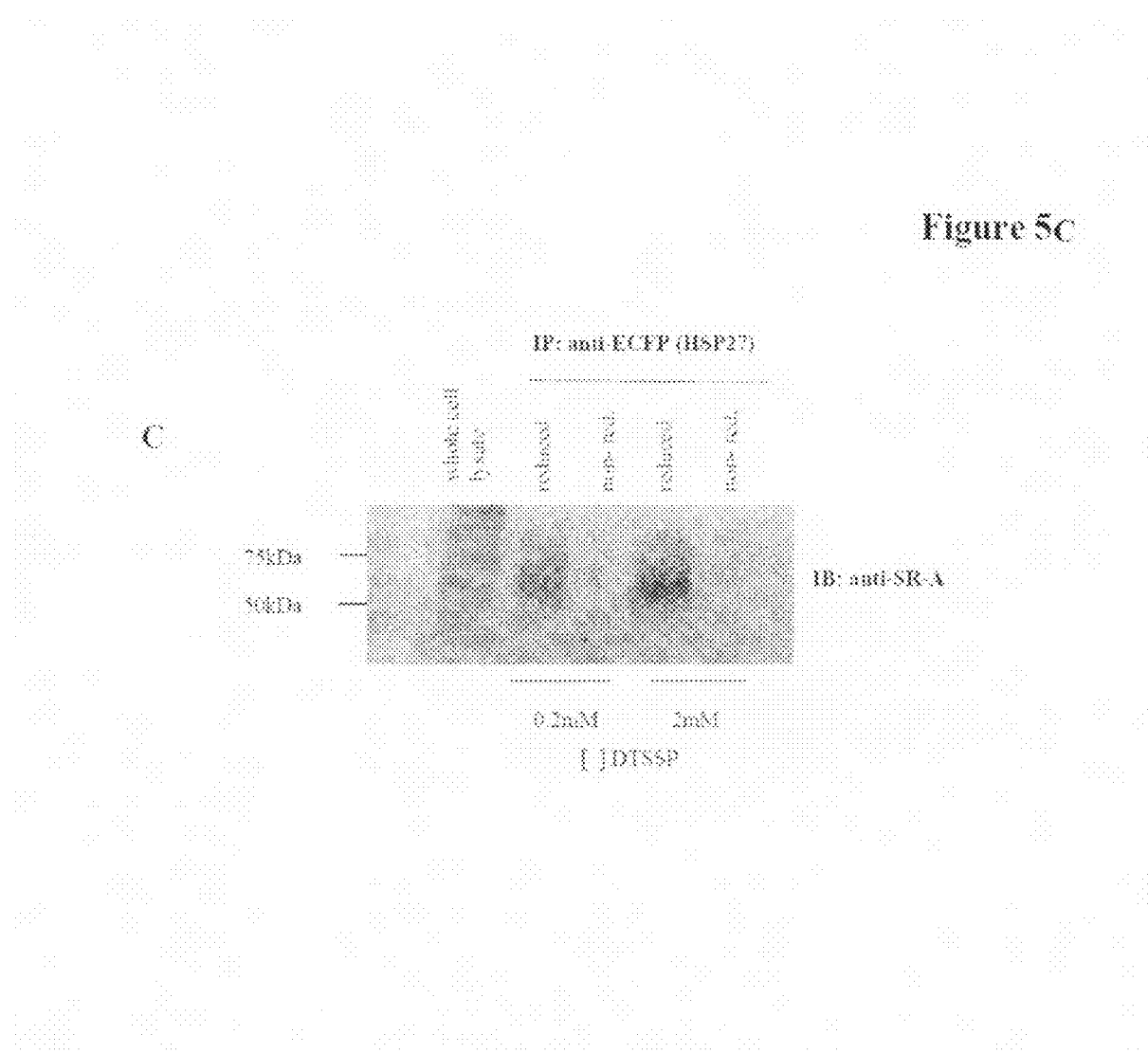

US 8,343,915 B2

USE OF HEAT-SHOCK PROTEIN 27 FOR CARDIOVASCULAR DISEASE PREVENTION AND TREATMENT

CROSS-REFERENCE TO RELATED APPLICATIONS

The present application claims the benefit of priority from U.S. provisional patent application Ser. No. 60/955,210, filed Aug. 10, 2007, the entire contents of which are herein incorporated by reference.

FIELD OF THE INVENTION

The present invention relates generally to cardiovascular disease. More particularly, the present invention relates to a method of preventing or treating cardiovascular disease using heat shock protein 27.

BACKGROUND OF THE INVENTION

Heat shock proteins are involved in a wide variety of processes, both physiological and pathological. Heat shock protein 27 (HSP27) is a member of the small heat shock protein family, which comprises members ranging from 15 to 30 kDa in size and which may be phosphorylated or oligomerized under various conditions. HSP27 is principally described as an intracellular chaperone capable of binding and stabilizing the actin cytoskeleton in response to stress. In addition, HSP27 can bind cytochrome c and prevent downstream caspase activation, making it a potent anti-apoptotic protein. More recently, it was discovered that HSP27 can interact with estrogen receptor β and reduce transcriptional signaling through the estrogen response element[1]. Although multi-faceted, the functions described for HSP27 have been solely thought to be within the confines of the cell membrane; however, extracellular release of HSP27 may be regulated and may have important effects on steps leading to the development of atherosclerosis.

While the role of estrogens in atherosclerotic coronary artery disease has enjoyed intense scrutiny over the past two decades or more, recent reappraisals of clinical trials and new experimental data strongly argue for a second look at the role of not only "hormone replacement therapy" (HRT), but also novel hormone manipulation strategies for the prevention/attenuation of atherosclerosis. There are several important caveats to clinical studies of HRT that help explain the absence of the expected cardiovascular benefits of HRT in post-menopausal women[2-4]. A principal deficiency of these studies is the late introduction of HRT to women, who, for example, in a Women's Health study, were on average 7 years post-menopausal before HRT was commenced[5, 6]. Many of these women may have been susceptible to the potential ravages of atherosclerosis while deficient of ovarian hormones in the initial years post-menopause. Hence, when HRT was introduced, it may have been too late to derive an "atheroprotective" (or reversal of atherosclerosis) effect.

The biological effects of estrogen are mediated by at least two cellular receptors: ER alpha (ERα) and ER beta (ERβ) that belong to the classical steroid hormone receptor superfamily. When activated, the receptors translocate to the nucleus and modulate transcriptional activity through interactions with estrogen response elements (EREs). These receptors also participate in signaling cascades at the cell membrane, suggestive of a function entirely independent of gene regulation[7]. Structurally, ERα and ERβ are subdivided into several functional domains including ligand binding, DNA binding, and both ligand-independent (AF-1) and ligand-dependent (AF-2) activation domains. While the two receptors share considerable structural similarities, they derive functional specificity via differential tissue expression patterns and regions of structural diversity (e.g. the A/B domain where there is only 30% sequence identity between ERβ and ERα)[8, 9]. Moreover, ER ligand complexes produce different effects in different cells due to variable expression of co-regulatory proteins (e.g. co-activators and co-repressors). Indeed, in some instances the physiological and pathophysiological response to hormones may reside with these co-regulatory molecules, rather than solely with the receptors themselves.

Approximately 300 nuclear receptor (NR) associated proteins are known, typically as a result of yeast two hybrid screens that employ the NR as "bait" (cf. review by Smith and O'Malley)[10]. In general, these proteins do not bind DNA directly, but instead facilitate the interaction of hormone receptors with DNA and other structural proteins—ultimately serving to facilitate (activator) or hinder (repressor) the activation of transcription.

For a variety of reasons ERβ has emerged as a key receptor in the vessel wall. For example, the expression of ERβ mRNA is markedly up-regulated after vascular injury in male arteries[11, 12]. Moreover, in male arteries, ERβ is the predominant receptor expressed in the intima, media and adventitia, and its expression correlates with the degree of calcification—a marker of severe atherosclerosis. Therefore, ERβ appears to play an important yet unidentified role in the progression of atherosclerosis. Yeast two-hybrid analysis revealed that HSP27 is an ERβ associated protein. HSP27 attenuated ERβ transcriptional activity preserved endothelial cell homeostasis, and normal volunteers had >3-fold higher serum levels than those patients with angiographic evidence of coronary artery disease.

It has been observed that HSP27 may be a potential biomarker for atherosclerosis, with expression of HSP27 diminishing with the progression of disease[1, 13, 14]. Serum levels of HSP27 have been shown to be attenuated in patients with atherosclerosis compared to healthy individuals[13]. HSP27 may be involved in long term vessel wall homeostasis that is then lost with the progression of atherosclerosis. Although the mechanisms by which HSP27 may be "atheroprotective" are not yet elucidated, many believe that analogous to its effects in other tissues (e.g. nerve, gastromucosal and myocardium) it protects the vessel wall from stressful stimuli and prevents apoptosis[15, 16]. While this may in part explain why HSP27 levels have been shown to be acutely increased in the serum following myocardial ischemia[14], HSP27 also appears to be involved in the long-term maintenance of vessel wall homeostasis that unfortunately may be lost with the progression of CAD.

It is, therefore, desirable to provide a method for preventing or treating cardiovascular disease using HSP27.

SUMMARY OF THE INVENTION

It is an object of the present invention to obviate or mitigate at least one disadvantage of previous methods of preventing or treating disease, particularly cardiovascular disease.

In a first aspect, the present invention provides a method for preventing or treating cardiovascular disease in a subject comprising administering to said subject heat shock protein 27 (HSP27), a co-factor, variant or analogue thereof. The cardiovascular disease can be atherosclerosis, and more particularly selected from the group consisting of coronary atherosclerosis, peripheral vascular disease and neo-intimal formation, for example. Surprisingly, HSP27 has been found to be atheroprotective.

HSP27 modulates cholesterol trafficking and mediators of inflammation. In particular, it has been surprisingly found that extracellular HSP27 may provide some degree of sex-specific protection against the development of disease. This may be due in part to its ability to bind the scavenger receptor-A and prevent uptake of atherogenic lipid (e.g. acytelated low-density lipoprotein or acLDL) as well as attenuate inflammation.

Administration of one or more types of estrogen (for example, 17-β-estradiol), specific estrogen receptor modulators or related compounds may contribute to an increase in HSP27 expression and, thus, a possible therapeutic effect in reducing atherosclerosis.

In another aspect, there is provided a kit for preventing or treating cardiovascular disease, the kit comprising heat shock protein 27, a variant, a co-factor, or analogue thereof, and instructions for use in preventing or treating cardiovascular disease.

The present invention also provides a pharmaceutical composition comprising heat shock protein 27, a co-factor, variant or analogue thereof. The composition may further comprise a pharmaceutically-acceptable diluent or carrier. The pharmaceutical composition is particularly suitable for treating or preventing cardiovascular disease as described herein.

In another aspect of the present invention, there is provided a method for preventing or treating cardiovascular disease in a subject comprising administering to said subject a therapeutically effective amount of an estrogen receptor agonist, antagonist, co-factor, or analogue thereof, such that heat shock protein 27 expression is modulated. A pharmaceutical composition comprising an estrogen receptor agonist, antagonist, co-factor, variant or analogue thereof, for use in treating or preventing cardiovascular disease, such that heat shock protein 27 expression is modulated, is also contemplated.

In one embodiment, the estrogen receptor is ERβ; however estrogen receptors may be involved. As one example, an estrogen receptor agonist is an estrogen, such as 17-β-estradiol.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIG. 4 illustrates secretion of HSP27 from macrophages in response to estrogen and acLDL. FIG. 4A shows macrophages treated with 100 nM 17β-estradiol (E2) for 24 hours. FIG. 4B is a Western blot showing macrophages treated in culture with 100 nM E2 for increasing times. FIG. 4C is a Western blot which shows that macrophages were treated in culture with increasing concentrations of acLDL (0-100 µg/ml) FIG. 4D is a Western blot showing increased HSP27 secretion after treatment of acLDL and/or E2. FIG. 4E is a Western blot following estrogen treatment. FIG. 4F is a Western blot following treatment with acLDL. FIG. 4G shows co-localization of HSP27 and the lysosome (LAMP1) after treatment with estrogen in macrophages. FIG. 4H shows J774 cells transfected with HSP27-ECFP (pseudo-coloured green) were treated with 100 µg/ml acLDL for either 1 hour (middle panel) or 24 hours (bottom panel) in the presence of Lysotracker red.

FIG. 5 shows extracellular HSP27 co-localizing with the scavenger receptor A (SR-A) on the surface of macrophages. FIG. 5A shows the effects of recombinant HSP27 (5 µg/ml) administration to macrophages for 2 hours at 4° C. FIG. 5B shows macrophages from SR-A null mice incubated with recombinant HSP27. FIG. 5C illustrates HSP27-ECFP secreted in response to acLDL and applied to naïve macrophages.

In FIG. 8A, peritoneal macrophages harvested from apoE$^{−/−}$ HSP27$^{o/e}$ and apoE$^{−/−}$ mice were plated on type I collagen. In FIG. 8B cell nuclei were stained and counted. FIG. 8C shows peritoneal macrophages as in FIG. 8A subject to CytoSelect™ migration assay for 24 hours and quantified.

DETAILED DESCRIPTION

Figure 1:
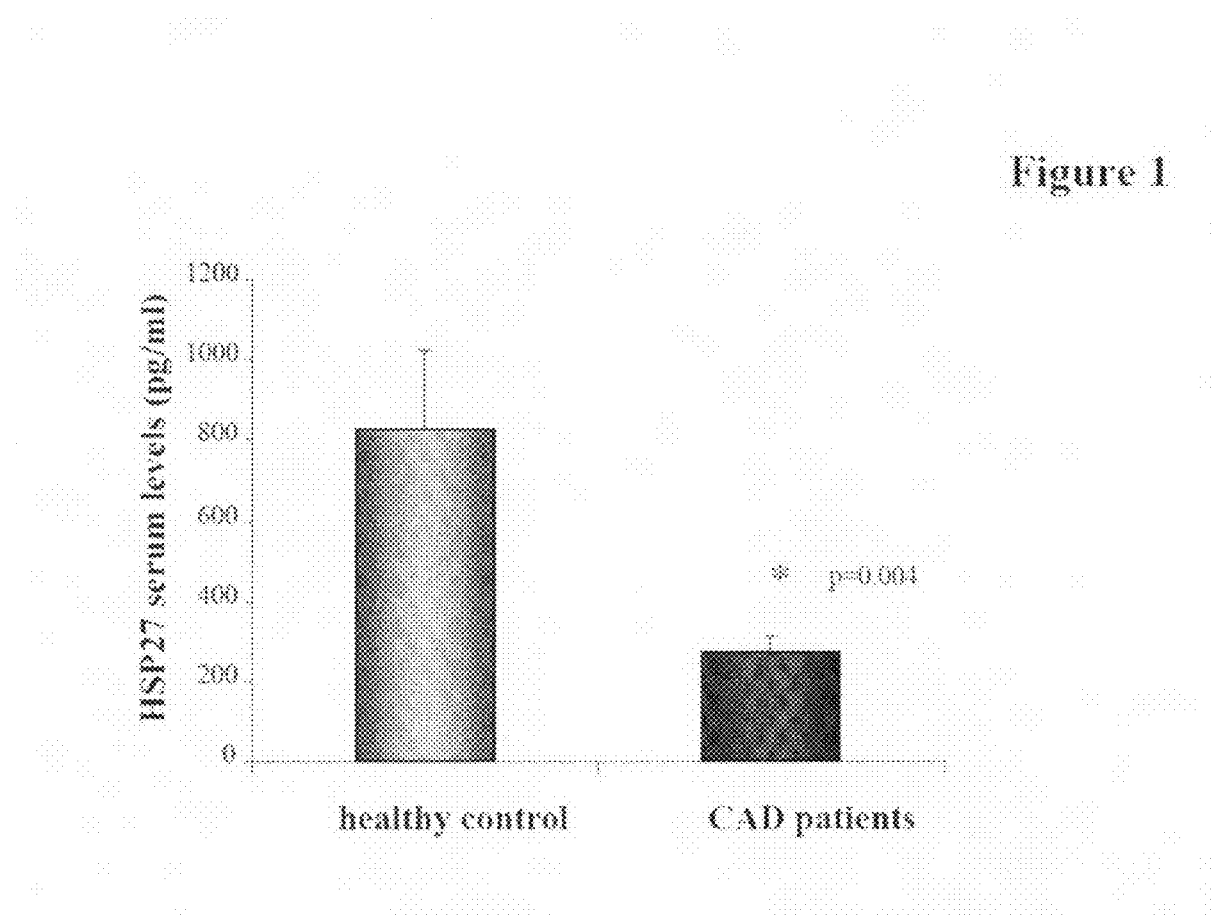
FIG. 1 shows HSP27 serum levels.

Generally, the present invention provides a method for preventing or treating cardiovascular disease in a subject. More particularly, the present invention provides a method for preventing or treating cardiovascular disease in a subject comprising administering to said subject a therapeutically effective amount of heat shock protein 27 (HSP27), a co-factor, variant or analogue thereof. The cardiovascular disease can be atherosclerosis, and more particularly coronary atherosclerosis, but also other more peripheral forms of atherosclerosis (e.g., involving the carotid or other peripheral arteries, such as in peripheral vascular disease), or in neointimal formation. In one embodiment, the subject is a female subject, such as a human female subject; however, this approach to the detection and treatment of subjects can also be applied to human male subjects.

Similarly, the present invention provides a pharmaceutical composition comprising heat shock protein 27, a co-factor, variant or analogue thereof, optionally together with a pharmaceutically-acceptable diluent or carrier. The present invention also contemplates a kit for preventing or treating cardiovascular disease, the kit comprising heat shock protein 27, a variant, a co-factor, or analogue thereof, and instructions for use in preventing or treating cardiovascular disease. The kit can be used for preventing or treating cardiovascular disease, particularly atherosclerosis, and more particularly coronary atherosclerosis, but also other more peripheral forms of atherosclerosis (e.g., involving the carotid or other peripheral arteries).

In another aspect of the present invention, there is provided a method for preventing or treating cardiovascular disease in a subject comprising administering to said subject a therapeutically effective amount of an estrogen receptor agonist, antagonist, co-factor, or analogue thereof, such that heat shock protein 27 expression is modulated. A pharmaceutical composition comprising an estrogen receptor agonist, antagonist, co-factor, variant or analogue thereof, for use in treating or preventing cardiovascular disease, such that heat shock protein 27 expression is modulated, is also contemplated.

As used in the present application, a "co-factor" can be any natural or artificial endogenous or exogenous molecule, such as a nucleotide, protein, chemical compound, adjuvant or the like, which a) binds to, associates with or interacts with an estrogen or HSP27, or an estrogen or HSP27 variant or analogue; b) binds to or assists with the binding of an estrogen or HSP27 to a receptor, either intra- or extracellularly; or c) binds to, associates with or interacts with an estrogen receptor including, but not limited to, ERβ.

As used in the present application, "cardiovascular disease" refers to any disease associated with the heart, brain, or vasculature, or any organ or tissue in communication with the vasculature. Particularly, cardiovascular diseases of interest in the present invention are those which are associated with the arterial vasculature including, but not limited to, carotid, coronary and/or peripheral arteries (e.g., "restenosis" after balloon angioplasty and/or stent implantation, and transplant vasculopathy).

As used in the present application, a "variant" can include a modified molecule, such as a nucleotide or protein. Suitable variants can include molecules which have been methylated, for example.

As used in the present application, an "analogue" is a molecule, such as an HSP27 nucleotide or protein sequence, which has been modified by insertion, deletion or substitution of one or more nucleotide or amino acid residues, such that the function of the molecule is maintained.

As used herein, "modulation" can refer to any induced modification on a molecular pathway such as, but not restricted to, upregulation or downregulation of gene expression, protein translation, cell signalling or other process.

EXAMPLES

Serum Collection

Plasma was collected from healthy controls (n=9) and patients with angiographic evidence of coronary artery disease (n=25) in accordance with the University of Ottawa Heart Institute Research Ethics Board. There were 21 males and 13 females with a mean age of 65±3 years, and 61±8 years, respectively. For mice, serum samples were collected at baseline (before the commencement of high-fat diet), and after 2 and 4 weeks of high-fat diet. Plasma and serum was stored at −80° C. until further use.

Enzyme Linked Immunosorbent Assay

Plasma levels of HSP27 were measured using an ELISA specific to human HSP27 (Calbiochem, San Diego, Calif.). A total of 50 µl of human plasma was assayed from both healthy controls and patients with CAD according to the manufacturer's protocol. A standard curve of known amounts of HSP27 was constructed with each assay. For mouse samples, serum was diluted 1:10 in dilution buffer, and assayed according to the manufacturer's protocol. This assay was found to have no cross-reactivity with mouse HSP25.

Mouse Model

Mice over-expressing human HSP27 ($HSP27^{o/e}$) on a C57BL10/CBA background were provided by Imperial College London, and were maintained by continuously backcrossing with C57BL10/CBA mice. $HSP27^{o/e}$ females were crossed with $apoE^{-/-}$ males to generate $apoE^{+/-}HSP27^{o/e}$ mice, which were crossed again to $apoE^{-/-}$ mice to generate $apoE^{-/-}$ $HSP27^{o/e}$ (n=6 males and n=9 females) and $apoE^{-/-}$ (n=6 males and n=9 females) littermates. All mice were tail-clipped and genotyped using previously described protocols[17] Mice were fed a normal chow diet until 6 weeks of age, wherein they received high-fat diet (1.25% cholesterol, 15.8% fat; Harlan Teklad, Madison, Wis.) for 4 weeks. Scavenger receptor knock out mice (SR-A KO) were used for collection of peritoneal macrophages at 12 weeks of age.

Cell Culture

Mouse peritoneal macrophages were obtained from peritoneal lavage with 9 ml sterile PBS. Cells were centrifuged and washed twice with PBS and resuspended in culture medium before counting and plating in 24-well plates. Peritoneal macrophages and J774 mouse macrophages were maintained in Dulbecco's Modified Eagle Medium (DMEM, Invitrogen, Burlington, ON) supplemented with 10% fetal bovine serum (FBS, Wisent, Saint-Jean-Baptiste de Rouville, QC), penicillin-streptomycin (Invitrogen), and fungizone (Invitrogen). acLDL was obtained from Intracel (Frederick, Md.), and DiI-labeled acLDL was obtained from Invitrogen. Fucoidan was obtained from Sigma-Aldrich (Oakville, ON). Lysotracker® Red was obtained from Invitrogen. Recombinant HSP27 was purchased from Stressgen (Ann Arbour, Mich.).

Transfections

J774 cells were transfected using Fugene HD transfection reagent (Roche, Laval, QC) as per the manufacturer's instructions. Cells were grown to 90% confluence on coverslips and transfected at a ratio of 2:3 (DNA:reagent) with HSP27-ECFP (pECFP-C1 was obtained from Clontech) for 24 hours before any treatment was initiated.

Western Blotting

Cell lysates were obtained using a RIPA buffer [1% NP-40, 0.5% sodium deoxycholate, 0.1% SDS, Complete™ inhibitor in PBS]. Cells were washed twice with PBS, lysed in RIPA buffer, collected using a cell scraper, and placed on ice for 45 minutes. Cell debris was collected by centrifugation at 15,000×g for 20 minutes, and the supernatant containing the cellular protein was isolated. Protein was quantified using Bradford reagent (Sigma). For western blotting, 50 µg of whole cell protein was loaded onto a 10% SDS-PAGE gel and separated at 120V using gel electrophoresis. Protein was then transferred to a PVDF membrane (BioRad, Hercules, Calif.)

for 2 hours at 60V. Membranes were then subjected to western blotting using the following antibodies: anti-HSP27 (Santa Cruz, 1:200); anti-SR-A (Chemicon, 1:2000); anti-IL-1β (R&D, 1:500); anti-IL-10 (Santa Cruz, 1:200).

Immunolabeling

J774 cells treated with recombinant HSP27 (5 µg/ml) with or without fucoidan (10 µg/ml) were fixed with BD Cytofix (BD Biosciences, Mississauga, ON) and blocked with 2% bovine serum albumin (BSA) for 2 hours. Antibodies against human HSP27 (Chemicon, 1:200) and scavenger receptor A (Serotec, 1:200) were incubated overnight at 4° C. Visualization of substrates was done using secondary antibodies conjugated to fluoroscein (for HSP27) and Texas Red (for SR-A). Negative controls included incubation with control IgG and secondary antibody alone.

Cross-Linking and Immunoprecipitations

J774 cells were transfected with HSP27-ECFP as described above, and treated with 100 µg/ml acLDL for 24 hours. Conditioned media from these cells was applied to naïve (untransfected) macrophages for 2 h at 4° C. to allow HSP27 to bind the cell surface. Cross-linking was performed using 3,3'-dithiobis(sulfosuccinimidyl propionate) (DTSSP, Pierce, Rockford, Ill.) as per the manufacturer's instructions. Cells were harvested in immunoprecipitation buffer (1% Triton X-100, 150 mM NaCl, 10 mM Tris pH 7.4, 1 mM EDTA, 1 mM EGTA, 0.2 mM sodium vanadate, 0.2 mM PMSF, 0.5% NP-40 in PBS) and 100 µg of total protein was immunoprecipitated with 5 µg of anti-ECFP antibodies (A.V. peptide, BD Biosciences) overnight at 4° C. with shaking. Protein-G-agarose was added for 4 hours, following which cells were centrifuged at 14,000×g and washed four times in IP buffer. Finally, IP pellets were resuspended in SDS-PAGE loading buffer with or without β-mercaptoethanol to reverse the cross-linking (reduced and non-reduced, respectively) and subjected to western blotting.

Confocal Microscopy

Cells were grown on cover slips, and transfected as described above. Cells were fixed with BD Cytofix as directed by the manufacturer and mounted with Dako Fluorescent mounting media (Dako Cytomation, Mississauga, ON). Coverslips were visualized with an Olympus FluoView FV1000 confocal microscope (Olympus America Inc, Center Valley, Pa.) at 100× magnification, using sequential scanning to reduce any potential non-specific excitation of the different fluorophores.

Fluorescent acLDL Uptake

Cells were treated with Dil-acLDL (5 µg/ml) for 4 hours at 37° C., in the presence of recombinant HSP27 (5 µg/ml) and/or fucoidan (10 µg/ml). Cells were harvested by gentle cell scraping in 100 µl of PBS. Each sample was analyzed for acLDL fluorescence on a BMG PolarStar plate reader (excitation: 510 nm, emission: 570 nm) and normalized to total cell number using the Vi-Cell cell counter (Beckman Coulter, Mississauga, ON).

Cell Adhesion Assay

Peritoneal macrophages were harvested from apoE$^{-/-}$ mice and apoE$^{-/-}$ HSP27$^{o/e}$ mice as described above. Cells (1.6× 10$^5$) were plated on type I collagen-coated 35 mm-dishes in 10% FBS DMEM. After 2 hours of incubation at 37° C., cells were washed with PBS and fixed with 4% paraformaldehyde in PBS for 1 hr at 4° C. Cell nuclei were stained with Hoechst 33258 for 10 min at RT. Photos were taken under fluorescence microscopy at 10× magnification, and the number of attached cells was manually counted per high power field (HPF).

Cell Migration Assay

Peritoneal macrophages were harvested from apoE$^{-/-}$ mice and apoE$^{-/-}$ HSP27$^{o/e}$ mice as described above. Cells (5.0× 10$^4$) were plated in the top chamber of a CytoSelect™ 96-Well Cell Migration Assay (Cell Biolabs, San Diego, Calif.) in 0.1% FBS-DMEM. The bottom chamber contained 10% FBS-DMEM as a chemoattractant. The migration chamber was incubated at 37° C. overnight, and migrated cells were quantified using a fluorescent dye (as per the manufacturer's instructions) and the BMG PolarStar plate reader (excitation: 488 nm, emission: 520 nm).

Statistical Analysis

All data represent mean±SEM. Statistical significance was defined by p value <0.05 and is denoted by an asterisk (*).

Example 1

Expression of HSP27 In Vivo

It has been suggested that HSP27 can serve as a biomarker for both carotid atherosclerosis and acute coronary syndrome[14]. As shown in FIG. 1, patients suffering from stable coronary disease (as demonstrated angiographically by coronary stenosis greater than 50%) demonstrate a 3-fold reduction in circulating HSP27 levels in the serum when compared to healthy, age-matched controls (828±195 vs. 272±38 pg/ml; p≦0.05). A negative correlation coefficient of −0.90 was observed. Serum HSP27 levels from healthy controls are in the left column and patients with stable CAD are in the right column (*p=0.004). Thus, HSP27 expression in the serum appears to be reduced in stable CAD. Patients with stable CAD also had reduced HSP27 serum levels when compared to those suffering from acute coronary syndrome (ACS).

Example 2

Mouse Model of Atherosclerosis

Figure 2:
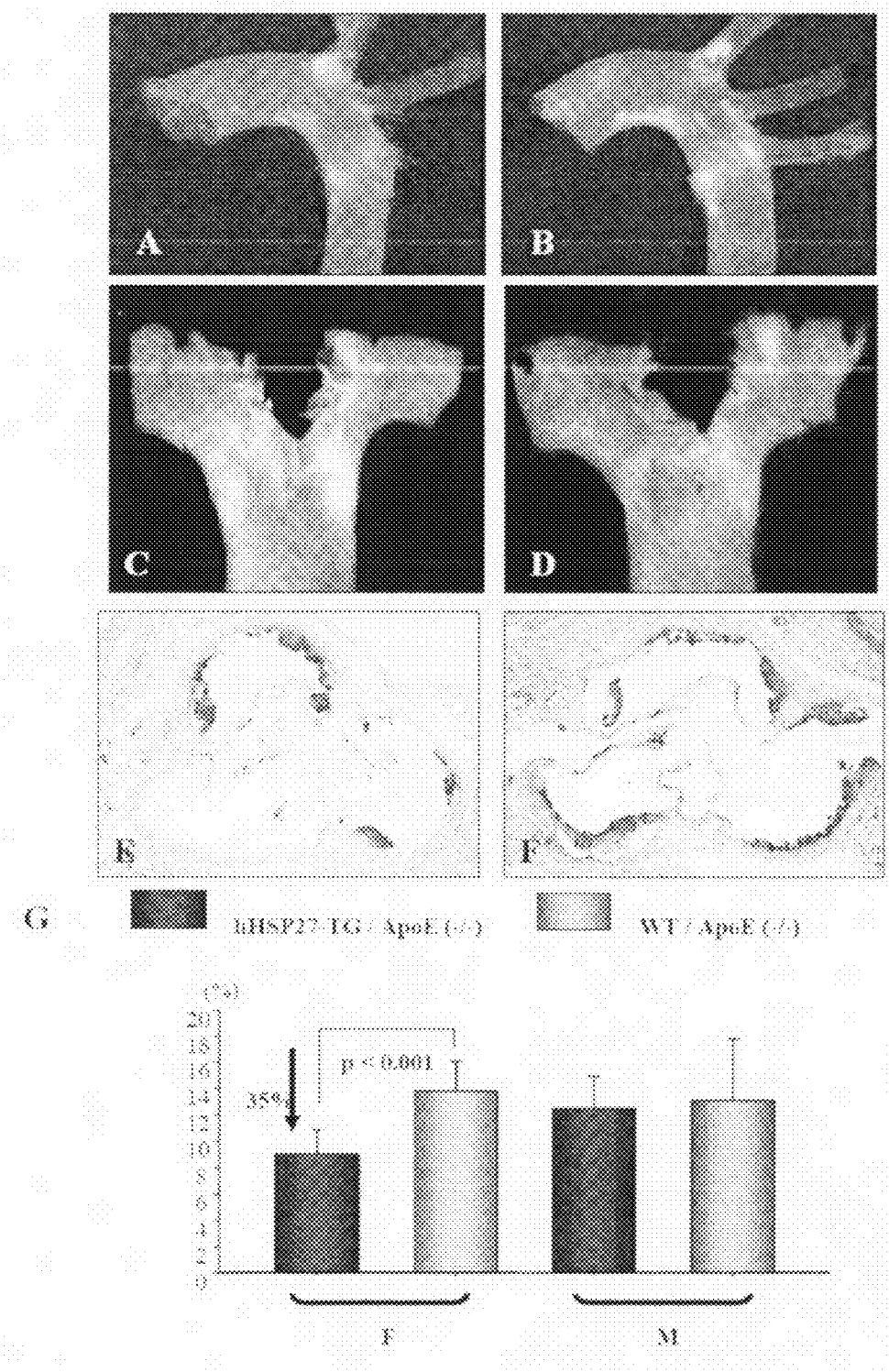
FIG. 2 shows the effects of HSP27 over-expression on atherosclerotic lesion size in mice after 4 weeks of high fat diet.

Using a mouse model of inflammatory atherosclerosis, the effects of over-expressing human HSP27 (HSP27$^{o/e}$) were examined in the development of disease. ApoE$^{-/-}$ HSP27$^{o/e}$ and apoE$^{-/-}$ mice were placed on a high-cholesterol diet for 4 weeks and euthanized at 10-weeks of age. There was no difference in mean bodyweight or length between HSP27Tg and WT mice, nor where there any differences between total serum cholesterol levels between these mice. FIGS. 2A to 2G show that the percentage aortic lesion area, measured by quantitative histomorphology of en face specimens, was reduced by 41% in the female HSP27Tg/apoE−/− vs. WT/apoE−/− mice (p<0.001). Total aortic en face atherosclerotic lesion area was analyzed in mice over-expressing human HSP27 (apoE$^{-/-}$ HSP27$^{o/e}$) (FIGS. 2A, 2C, 2E) and compared to their apoE$^{-/-}$ littermates (FIGS. 2B, 2D, 2F). Quantification of lesion area/total aortic area (FIG. 2G) demonstrates there was a 35% reduction in lesion burden in apoE$^{-/-}$ HSP27$^{o/e}$ female mice compared to apoE$^{-/-}$ (*p<0.001). Interestingly, there was no difference observed between male apoE$^{-/-}$HSP27$^{o/e}$ and WT/apoE−/− mice, suggestive of a role of ovarian hormones in the atheroprotective effects of HSP27. The serum of these mice was examined for circulating HSP27 levels using an ELISA.

Figure 3:
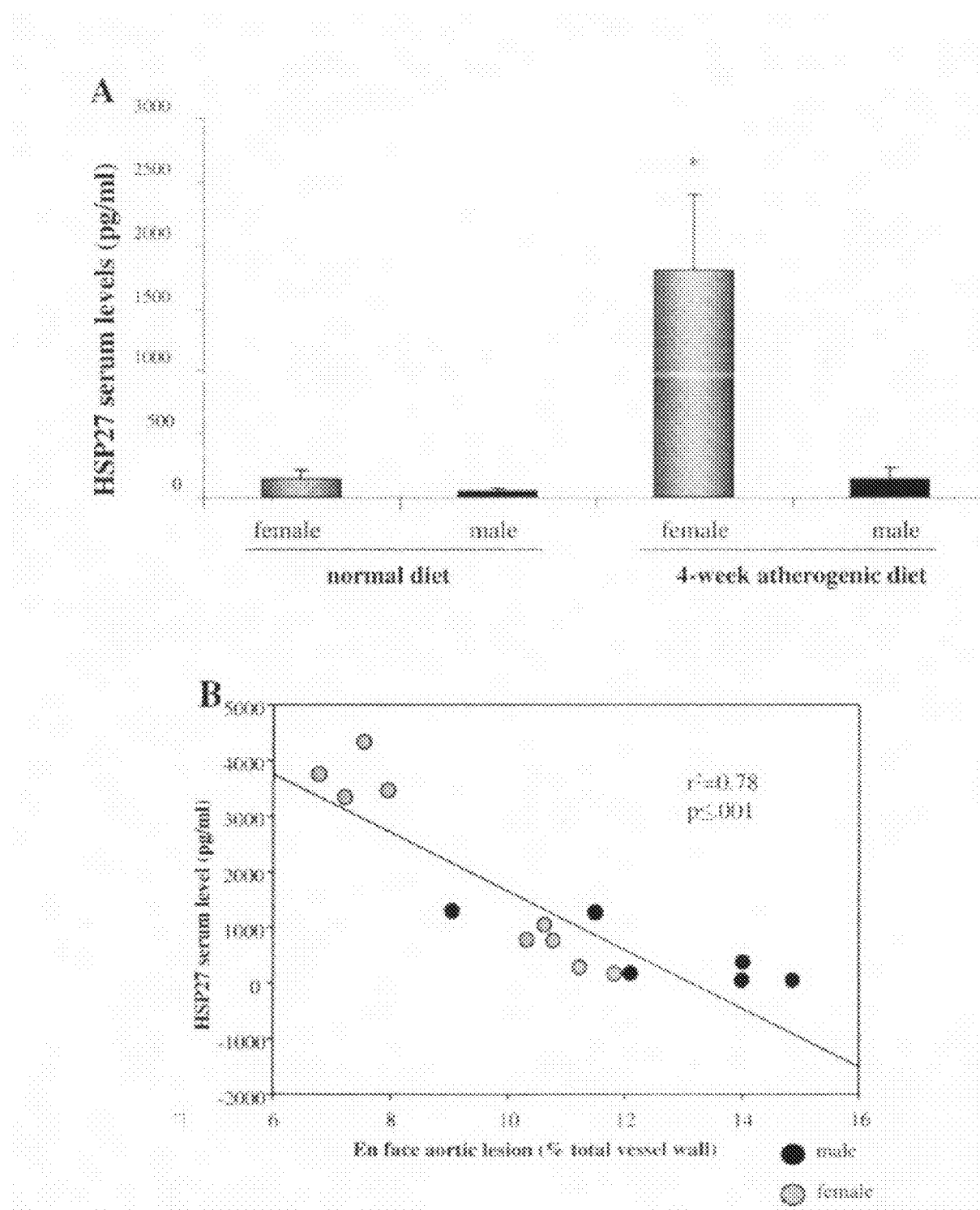
FIG. 3A shows HSP27 serum levels in response to an atherogenic diet.
FIG. 3B shows regression analysis comparing HSP27 serum levels with aortic en face lesion area in female mice.

FIG. 3A shows that in all mice fed a normal chow diet, there was little to no detectable HSP27 in the serum. However, following 4 weeks of a high-fat diet, female HSP27$^{o/e}$/apoE−/− mice had 10-fold higher circulating levels of HSP27 compared to male mice (p≦0.05). These were the same female mice that were offered a 41% relative protection from lesion development compared to their wild-type littermates—an effect that was not observed in the male mice. FIG. 3B shows that when circulating HSP27 levels were compared to total en face lesion area, there was a significant negative correlation between serum HSP27 levels and atherosclerotic lesion area ($r^2=-0.90$; $p<0.001$). Thus, female ovarian hormones may be involved in atheroprotective effects of HSP27.

Example 3

HSP27 Secretion In Vitro in Response to Estrogen and acLDL

As serum HSP27 levels inversely correlate with aortic lesion area in mice fed a cholesterol-enriched diet, and is 10-fold higher in females than in males, we determined in vitro whether HSP27 is released on stimulation with estradiol (E2) or atherogenic acetylated low-density lipoprotein (acLDL). Human macrophages (U937) were plated in replicates at a density of 1_106 per well and treated with estradiol or acLDL. Conditioned media was collected and before analysis for secreted HSP27, overall cell viability was measured using an LDH-release assay and revealed no difference in cell viability or membrane integrity between any of the treatments (data not shown). Treatment of macrophages with estrogen (E2) for 24 hours caused a dose-dependent increase in HSP27 release into the media compared to controls (FIG. 4A). Estrogen-induced HSP27 release also increased over time, with maximum secretion after 24 hours (FIG. 4B). Macrophages were subjected to increasing concentrations of acLDL (1 to 100 µg/mL) for 24 hours. HSP27 protein was detected by Western blot in conditioned media from cells treated with 100 µg/mL acLDL (FIG. 4C). The addition of acLDL to the media containing estrogen caused a further increase in HSP27 secretion when compared to estrogen or acLDL treatment alone, indicating that these 2 mechanisms of secretion may act synergistically (FIG. 4D). On treatment with estrogen, examination of intracellular protein levels revealed that HSP27 protein levels increased slightly in response to estrogen treatment, suggestive of an intracellular pool of HSP27 that is secreted without necessitating de novo protein synthesis (FIG. 4E).

On treatment with acLDL, there was a concomitant dose-dependent increase in intracellular HSP27 expression, then an apparent decrease corresponding to increased HSP27 protein release into the media (FIG. 4F). To examine the pathway of HSP27 secretion, we used 2 independent experiments: the first used human U937 macrophages treated with E2 and immunolabeled for HSP27 and a marker of the lysosomal membrane (LAMP1); second, mouse J774 macrophages were transfected with a fluorescently tagged HSP27 (HSP27-ECFP), and treated with acLDL in the presence of Lysotracker, which labels acidic organelles (ie, lysosomes) in live cells. Using both methods, we localized intracellular HSP27 in macrophage lysosomes after treatment with E2 or acLDL. Specifically, human macrophages treated with 100 nmol/L E2 overnight displayed colocalization of HSP27 (red) and LAMP1 (green; FIG. 4G). Similarly, mouse macrophages transfected with fluorescently-tagged HSP27 (green) treated with 100 µg/mL acLDL and incubated in the presence of Lysotracker (red) displayed HSP27 colocalization within lysosomes after treatment for 1 hour and 24 hours (merged image, FIG. 4H). Without estrogen treatment, HSP27 showed minimal colocalization with the lysosome (FIGS. 4G and 4H, bottom row). Cells transfected with empty ECFP alone with or without acLDL treatment did not show colocalization with the lysosome, indicating that HSP27-ECFP was not simply degraded and targeted to the lysosome (data not shown). These results indicate that HSP27 is found within secretory lysosomal-like vesicles in macrophages under conditions which stimulate its secretion (eg, on treatment with E2 or acLDL).

Example 4

Extracellular HSP27 Binding of the Scavenger Receptor-A In Vitro Results in Decreased acLDL Uptake and Inflammation As HSP27 is secreted not only in vitro by atherogenic lipids, but in vivo in response to high fat diet, extracellular HSP27 binding of a receptor on the surface of cells to exert its potential atheroprotective effects was examined. As is known in the prior art, members of the heat shock protein family bind a variety of cell surface receptors, including toll-like receptors and scavenger receptors[18-21]. Due to the observation that higher levels of HSP27 correlate with lower atherosclerotic lesion burden, extracellular HSP27 was examined for possible binding of the SR-A receptor—an important receptor for the uptake of atherogenic lipids and the progression of atherosclerosis[22, 23].

FIG. 5A shows immunolabeling studies which revealed that recombinant HSP27 is capable of binding the surface of macrophages, and co-localizes with SR-A. Immunolabeling of HSP27 (green) and SR-A (red) was visualized under confocal microscopy (top panel). Cells were also treated with an SR-A specific competitive ligand (fucoidan, 10 µg/ml) before administration of HSP27 (bottom panel). Co-localization is seen as a yellow colour. In the presence of fucoidan, a specific competitor for SR-A, HSP27 binding to SR-A was reduced, indicating that this interaction is specific. FIG. 5B shows that, in mouse macrophages from SR-A null mice, HSP27 binding to the cell surface was completely abolished. Macrophages from SR-A null mice were harvested and incubated with recombinant HSP27 (5 µg/ml) for 2 hours at 4° C. Immunolabeling was performed as described above.

Endogenous HSP27 secreted in response to acLDL was examined to determine if it was also capable of binding the SR-A. Conditioned media from macrophage whole cell lysates were transfected with HSP27-ECFP and treated with 100 µg/ml acLDL was applied to naïve, untreated macrophages at 4° C. for 2 hours to allow HSP27-ECFP to bind the cell surface. Cells were then treated with DTSSP, a reversible, membrane-impermeable cross-linking agent, to cross-link HSP27 to the cell surface. Immunoprecipitation was carried out using antibodies to the fluorescent tag (anti-ECFP) and cross-linked proteins were either reduced (to reverse cross-linking) or non-reduced (to maintain it), separated on an SDS-PAGE gel and subjected to immunoblotting.

FIG. 5C shows that using antibodies to SR-A, HSP27-ECFP secreted from cells treated with acLDL binds the scavenger receptor-A, under various concentrations of DTSSP. HSP27-ECFP secreted in response to acLDL was applied to naïve macrophages at 4° C. for 2 hours. Cells were crosslinked with increasing concentrations of DTSSP (0.1-2 mM) and immunoprecipitated using an antibody to ECFP.

Whole cell lysate from macrophages was also probed showing the detection of a ~50 kDa band corresponding to SR-A in these cells. This data confirms that indeed HSP27 binds specifically to SR-A both as an extracellular recombinant protein, and as a protein secreted in response to acLDL.

Foam cell formation is a hallmark process in the development of atherosclerosis, and prevention of lipid uptake by macrophages may serve to reduce overall lesion development and inflammation. If HSP27 can bind the SR-A in vitro, and there is an atheroprotective effect of HSP27 in vivo, HSP27 may prevent the SR-A from taking up atherogenic lipids such as acLDL and becoming foam cells. In support of this, mouse macrophages were cultured in vitro in the presence of fluorescently labeled acLDL for 6 hours, and acLDL uptake was measured using a fluorometer and normalized to total cell number.

Figure 6:
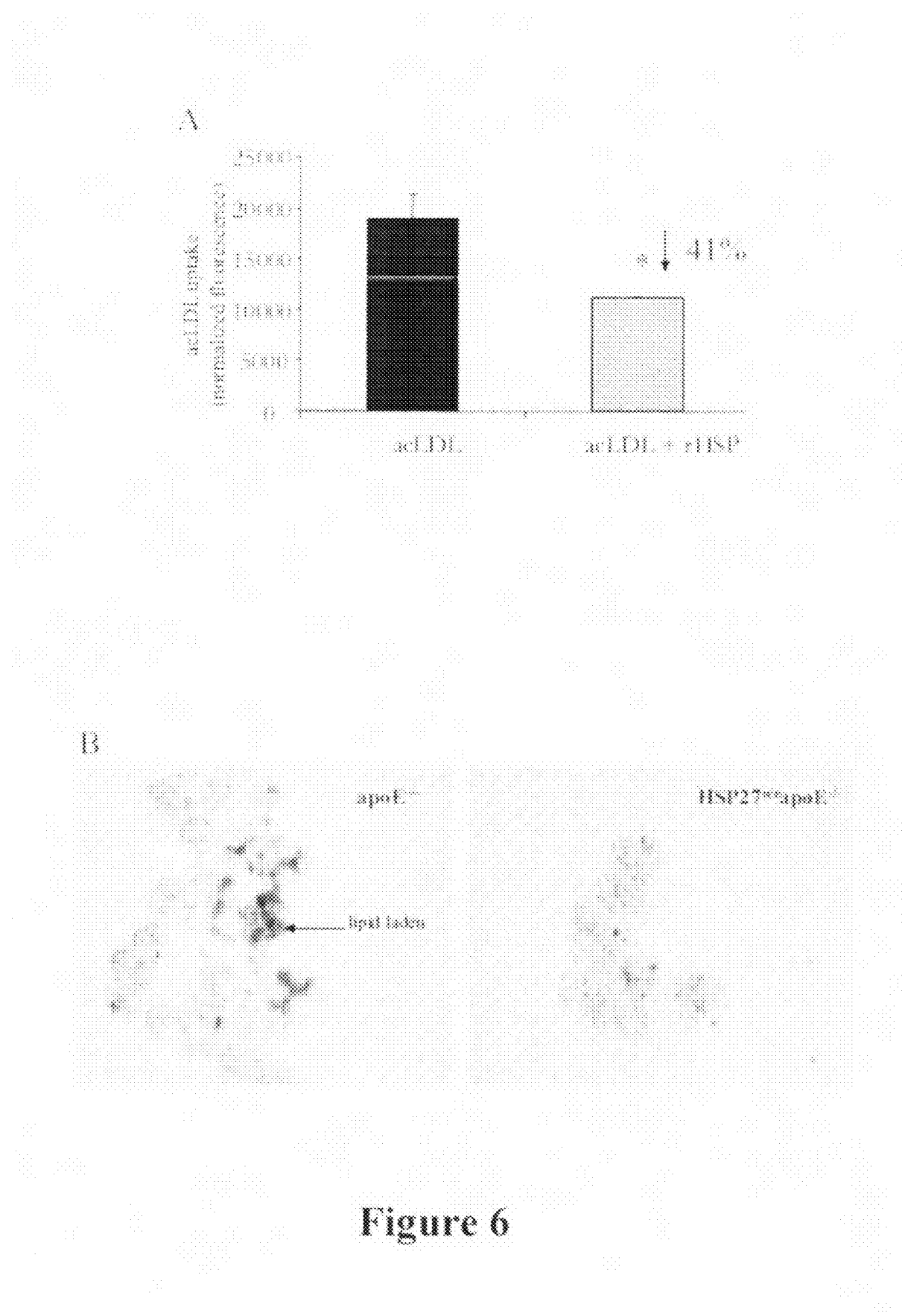
FIG. 6A illustrates extracellular HSP27 and its effects on uptake of acLDL by macrophages.
FIG. 6B shows decreased foam cell content in peritoneal macrophages from HSP27$^{o/e}$/apoE−/− mice compared to WT apoE−/− mice (3% vs. 21% lipid-laden cells).

FIG. 6A shows that when extracellular HSP27 was added to the culture media, there was a 41% reduction in acLDL uptake by macrophages ($p \leq 0.05$). Extracellular HSP27 inhibits uptake of acLDL by macrophages via the scavenger receptor A. Fluorescently labeled acLDL (5 ug/ml) was given to macrophages in the presence (right columns) or absence (left columns) of recombinant HSP27 (5 µg/ml). Cells were also treated with an SR-A specific competitor (fucoidan, 10 ug/ml) before administration of acLDL or HSP27. Fluorescent uptake was measured and normalized to total cell number. Fucoidan, a specific SR-A competitive ligand, was capable of inhibiting this process independently of the presence of HSP27, indicating that this reduction in acLDL uptake by HSP27 is likely via the SR-A. FIG. 6B shows decreased foam cell content in peritoneal macrophages from HSP27$^{o/e}$/apoE−/− mice compared to WT apoE−/− mice (3% vs. 21% lipid-laden cells).

Figure 7:
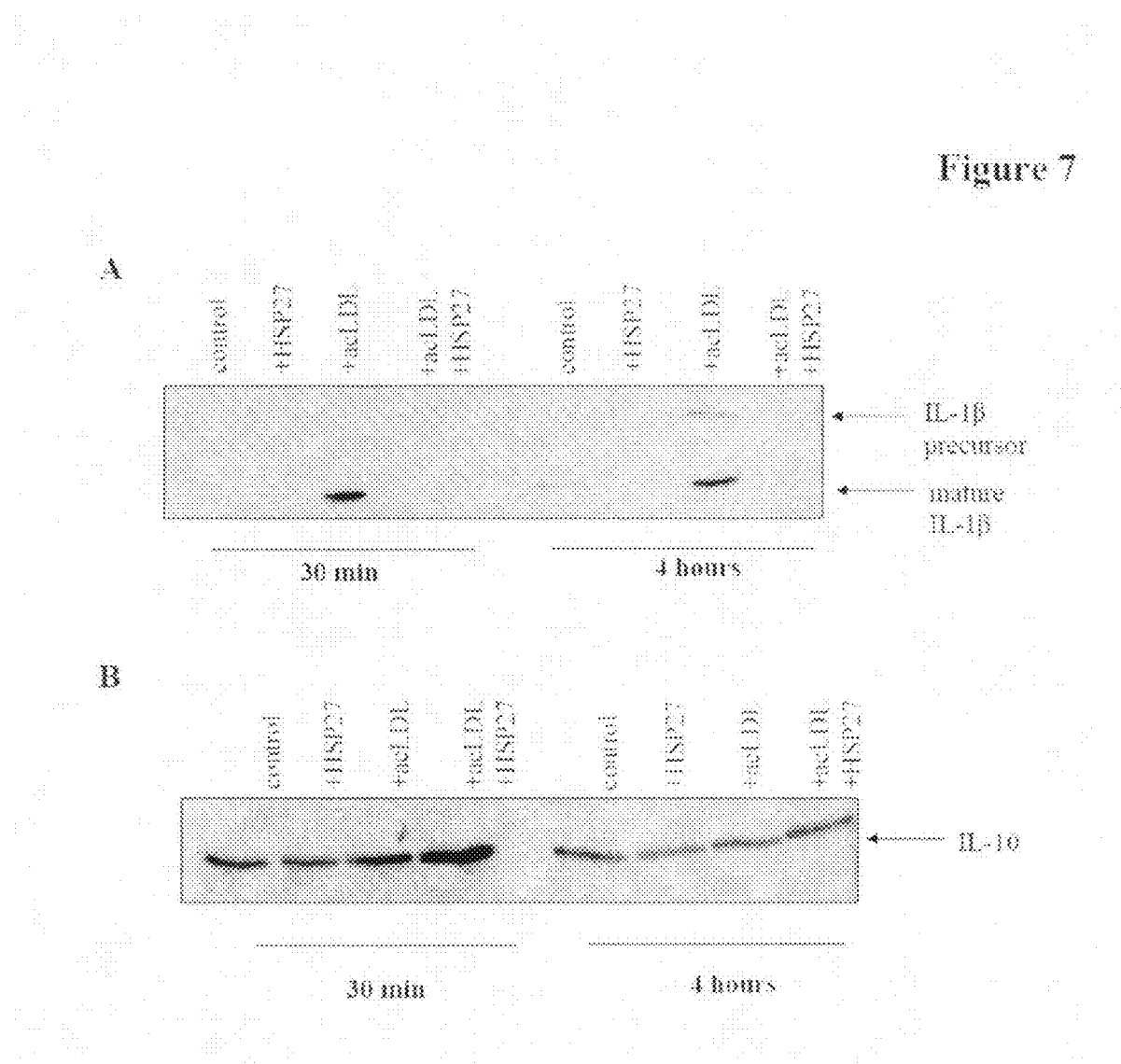
FIG. 7 shows the effects of extracellular HSP27 on the release of cytokines involved in the inflammatory response: IL-1β (FIG. 7A) and IL-10 (FIG. 7B).

FIG. 7 shows that extracellular HSP27 results in release of cytokines involved in the inflammatory response. Fluorescently labeled acLDL (5 ug/ml) was given to macrophages in the presence or absence of recombinant HSP27 (5 µg/ml). Conditioned media was collected after 30 minutes and 4 hours and subjected to western blotting for IL-1β (FIG. 7A) and IL-10 (FIG. 7B). Addition of HSP27 caused a decrease in the acLDL-induced secretion of IL-1β into the extracellular space.

Moreover, this reduction in acLDL uptake by HSP27 resulted in a considerable decrease in the acLDL-induced release of IL-1β by macrophages, a potent pro-inflammatory cytokine (FIG. 7A). Extracellular HSP27 also increased the released of the anti-inflammatory cytokine IL-10 (FIG. 7B). Thus, it appears that extracellular HSP27 is primarily an anti-inflammatory signaling protein. This is consistent with previous studies in monocytes.

In summary, in vitro studies of mouse macrophages in culture subjected to increasing concentrations of atherogenic lipid (acLDL) revealed that HSP27 is secreted by macrophages (lysosomal) in response to acLDL. The results suggest that HSP27 is secreted by macrophages in vitro in response to acLDL. HSP27 was observed to bind to the surface of macrophages and interact specifically with SR-A; in SR-A null mice, HSP27 binding to the cell surface was completely abolished. It was confirmed that HSP27 binds specifically to SR-A both as extracellular recombinant protein (HSP27-ECFP), and as a protein secreted in response to acLDL. Thus, the results suggest that extracellular HSP27 binds the scavenger receptor-A. Further, it was found that the reduction in acLDL uptake by HSP27 is via the SR-A on road to foam cell development. The reduction in acLDL uptake by HSP27 resulted in a considerable decrease in acLDL-induced release of IL-1β by macrophages, a potent pro-inflammatory cytokine, and an increase in IL-10, and anti-inflammatory cytokine. Thus, the results suggest that intracellular HSP27 prevents acLDL uptake by macrophages.

Example 5

HSP27 Over-Expression Reduces Cell Adhesion and Migration

Figure 8:
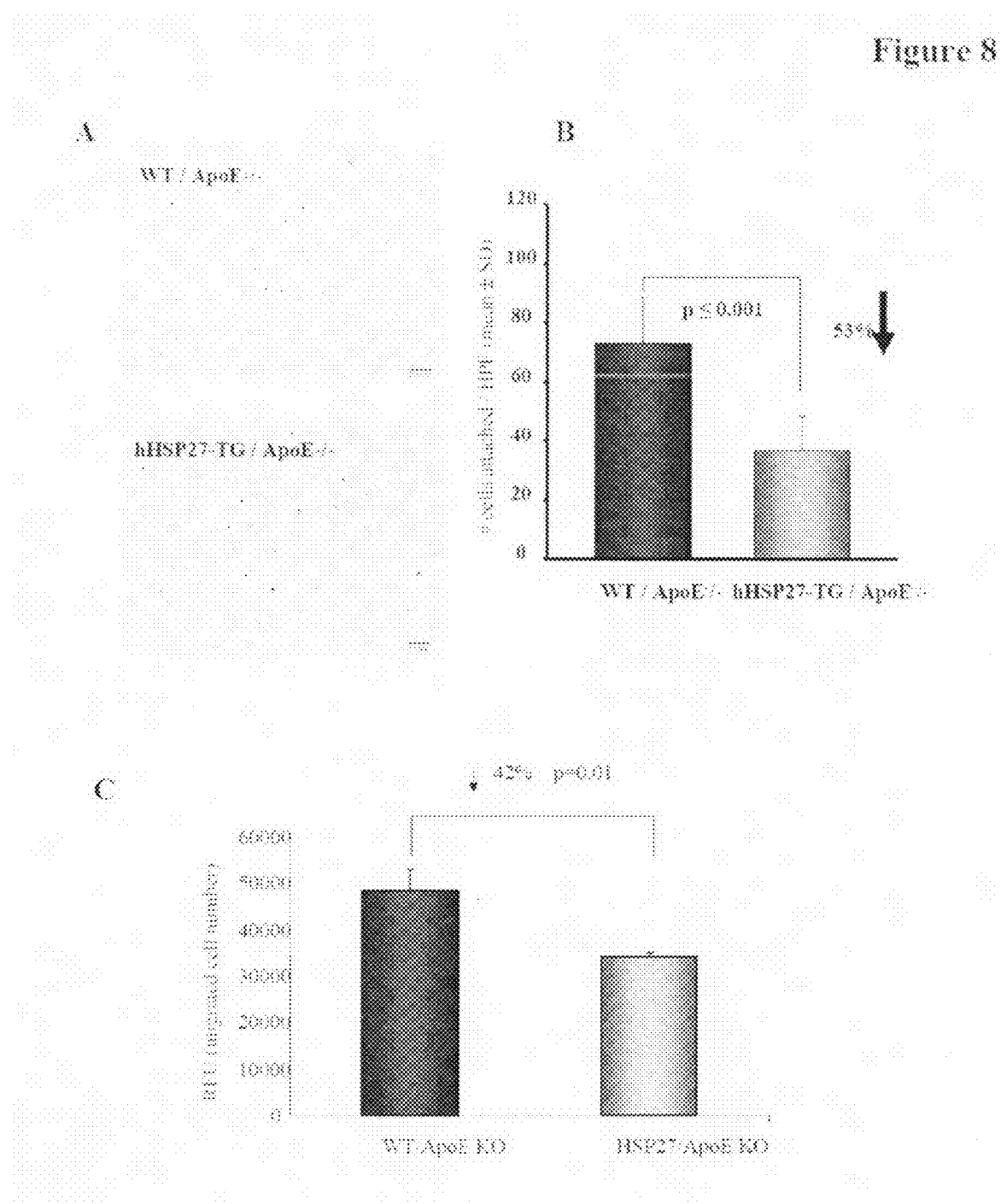
FIG. 8 illustrates the effects of HSP27 over-expression on macrophage adhesion and migration.

To further investigate how HSP27 might be protective against the development of atherosclerosis, peritoneal macrophages were harvested from HSP27$^{o/e}$/apoE−/− and WT apoE−/− mice after a high fat diet. FIG. 8 shows that HSP27 over-expression results in decreased macrophage adhesion and migration. Peritoneal macrophages harvested from apoE−/−HSP27$^{o/e}$ and apoE−/− mice were plated on type I collagen. After 2 hrs incubation, the cells were washed and fixed. Cell nuclei were stained with Hoechst 33258 and the number of cells per high power field (HPF) was manually counted. Peritoneal macrophages as in FIG. 8A were subject to CytoSelect™ migration assay for 24 hours, and quantified as total number of cells migrated towards 10% FBS. Cells were plated in culture on a collagen matrix, and allowed to adhere for 2 hours. As shown in FIGS. 8A and 8B, there was a 53% reduction in cell adhesion in HSP27$^{o/e}$/apoE−/− macrophages compared to WT apoE−/− ($p \leq 0.001$). Macrophages were also placed in a transwell migration chamber in serum-free media, and allowed to migrate towards 10% FBS overnight. FIG. 8C shows a 42% reduction in cell migration in HSP27$^{o/e}$/apoE−/− macrophages compared to WT ($p \leq 0.01$). Combined, these results indicate that macrophages from HSP27 over-expressing mice have a reduced ability to adhere and migrate, suggesting that in vivo these cells are less likely to incorporate into vascular lesions and exacerbate disease Thus, In vitro adhesion and migration experiments using peritoneal macrophages from HSP27 and WT mice after a high diet revealed that macrophages from HSP27 over-expressing mice have a reduced ability to adhere and migrate, suggesting that in vivo, these cells are less likely to incorporate into vascular lesions and exacerbate disease. The results suggest that HSP27 over-expression reduces cell adhesion and migration.

The methodologies used are described herein.

Example 7

Release of HSP27 and Interaction with Estrogen Receptors (ERs)

Figure 9:
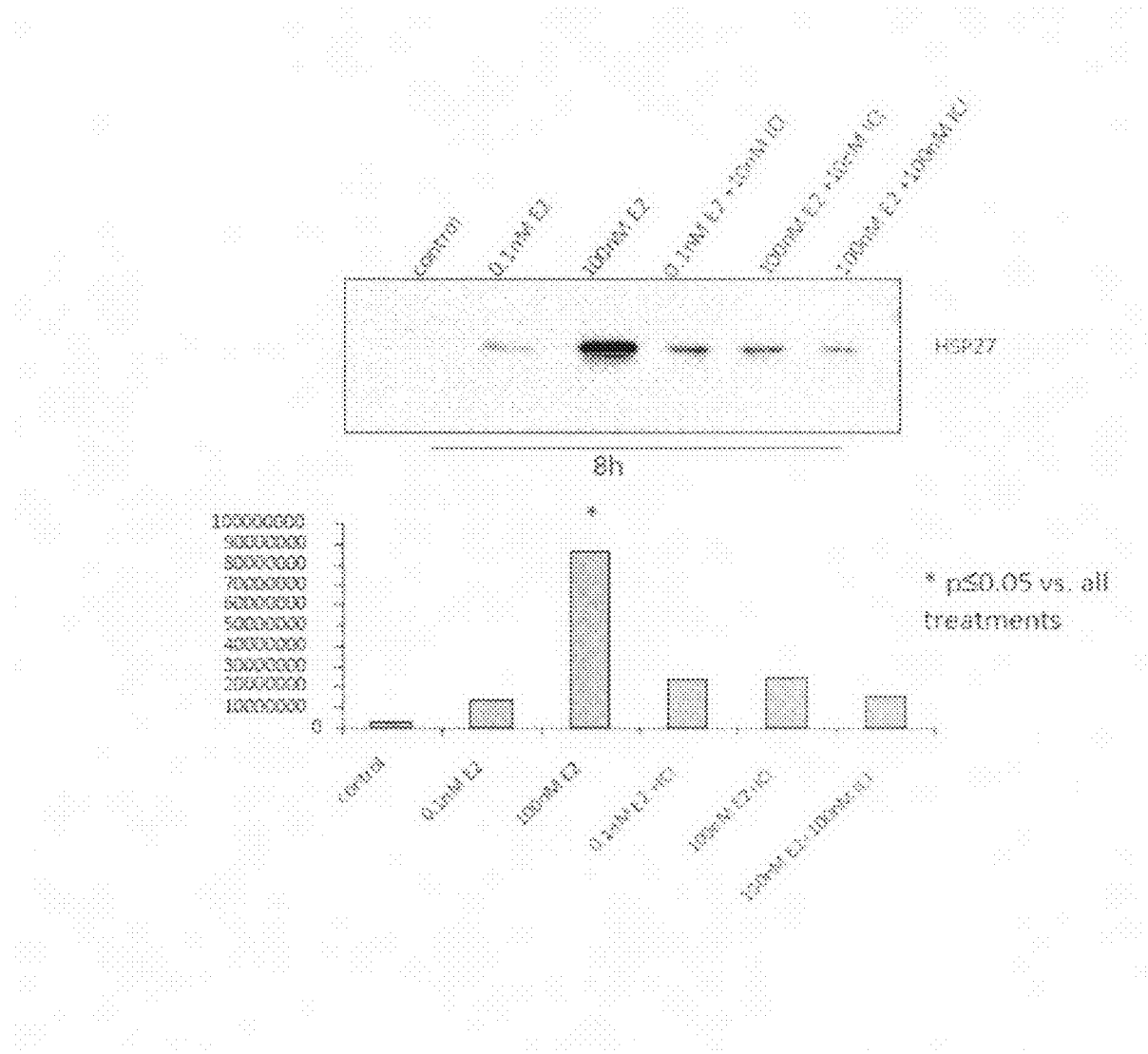
FIG. 9 shows a Western blot of HSP27 upon estrogenic stimulation of ERs.

FIG. 9 shows that HSP27 secretion may be dependent upon estrogenic stimulation of ERs. Human macrophages were treated with increasing concentrations of estrogen (E2; 0-100 nM) with or without increasing concentrations of the ER-antagonist ICI 182,780 (0-100 nM). HSP27 was detected in the extracellular space by Western blot. The bottom panel of FIG. 10 shows a quantification of the bands.

Figure 10:
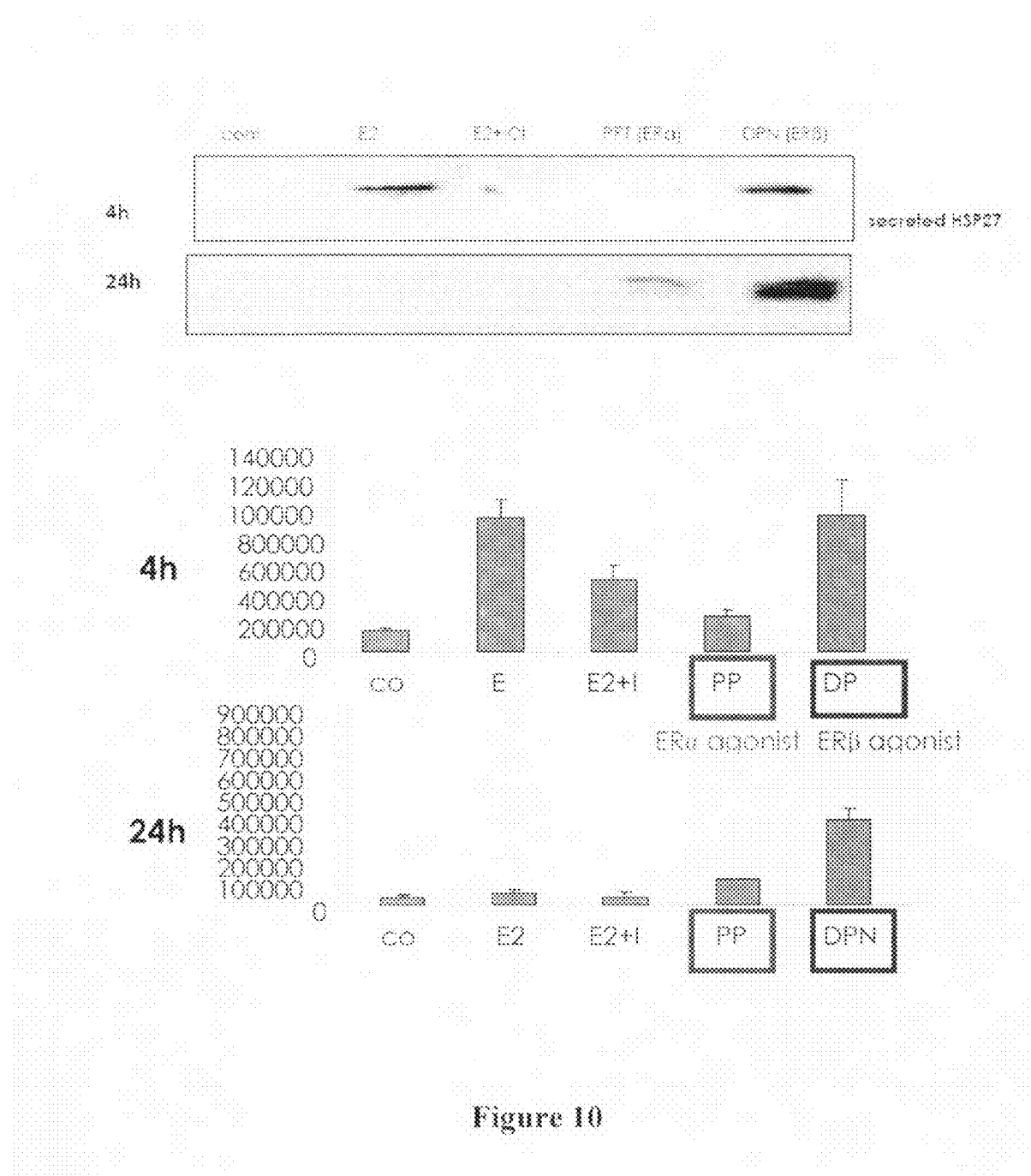
FIG. 10 shows a Western blot of HSP27 after stimulation of Erβ.

In FIG. 10, HSP27 secretion was shown to be enhanced upon stimulation of ERβ. Human macrophages were treated with estrogen (E2; 100 nM), an Era-specific agonist (PPT; 10 nM), or an Erβ-specific agonist (DPN, 1 nM) for either 4 h or 24 h. HSP27 was detected in the extracellular space by Western blot. The bottom panel of FIG. 10 shows the quantification of bands.

Figure 11:
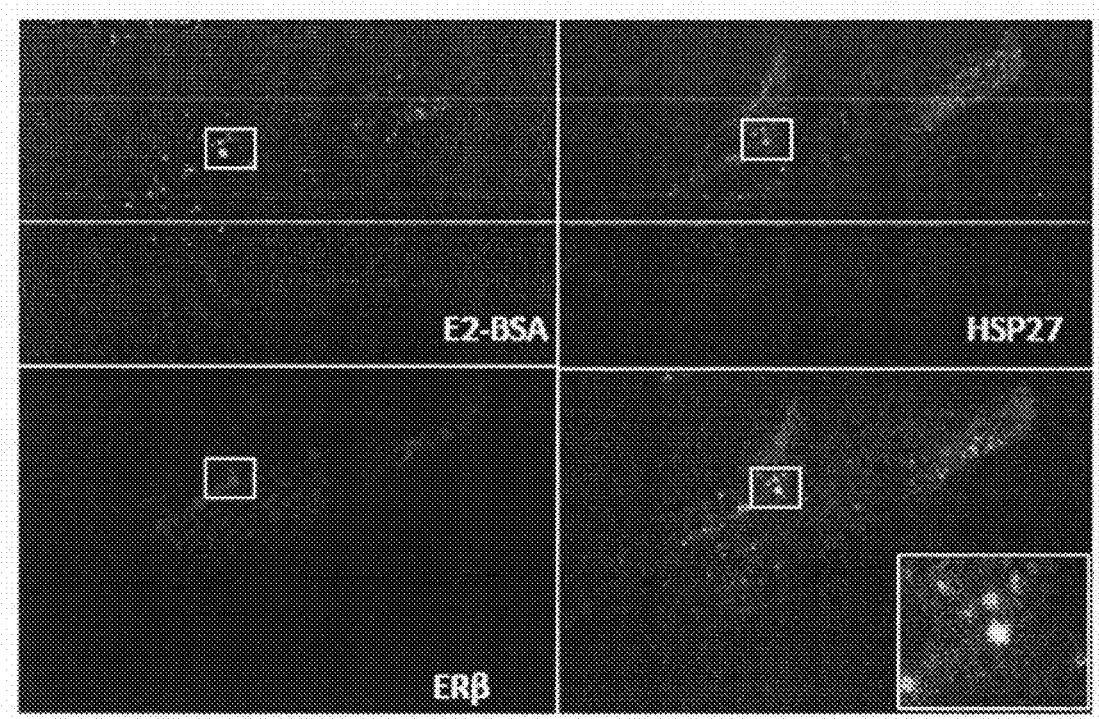
FIG. 11 illustrates the localization of HSP27 and Erβ to membrane-bound vesicles.

FIG. 11 shows an example of HSP27 and Erβ localizing to membrane-bound vesicles. Human macrophages were treated with E2-BSA (cell-impermeable E2) labeled with FITC, and immunolabeled for HSP27 and ERβ. The merged image shows HSP27 and Erβ colocalizing with vesicles at the membrane containing E2-BSA.

Figure 12:
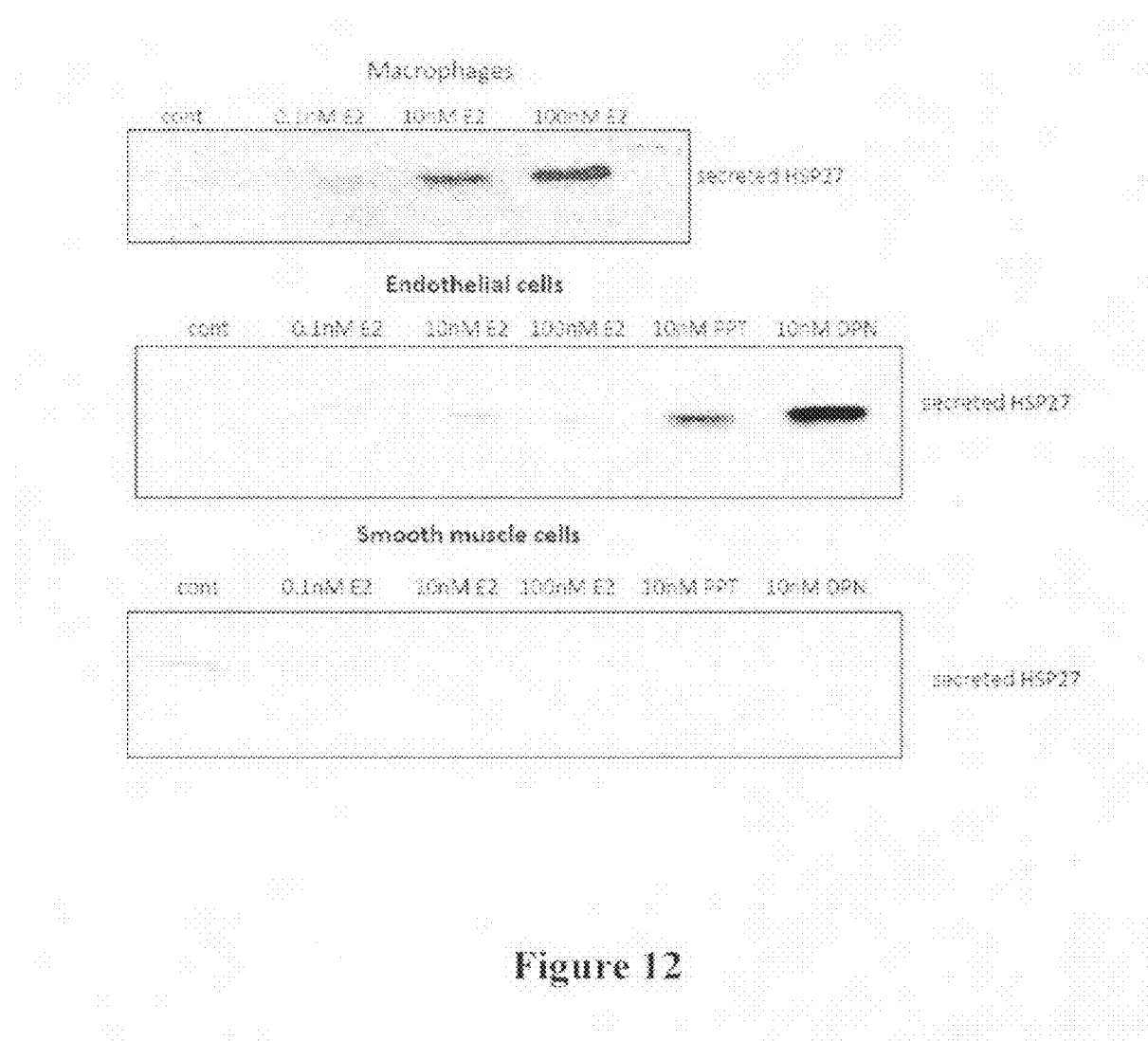
FIG. 12 shows a Western blot of HSP27 protein expression in macrophages, endothelial cells and smooth muscle cells.

FIG. 12 shows the release of HSP27 in a cell-type specific manner. Human macrophages, aortic endothelial cells and aortic smooth muscle cells were treated with estrogen (E2; 100 nM), an Era-specific agonist (PPT; 10 nM), or an Erβ-specific agonist (DPN, 1 nM) for 24 h. HSP27 was detected in the extracellular space by Western blot. Erβ stimulation appeared to cause an increase in HSP27 secretion from endothelial cells but not smooth muscle cells.

Figure 13:
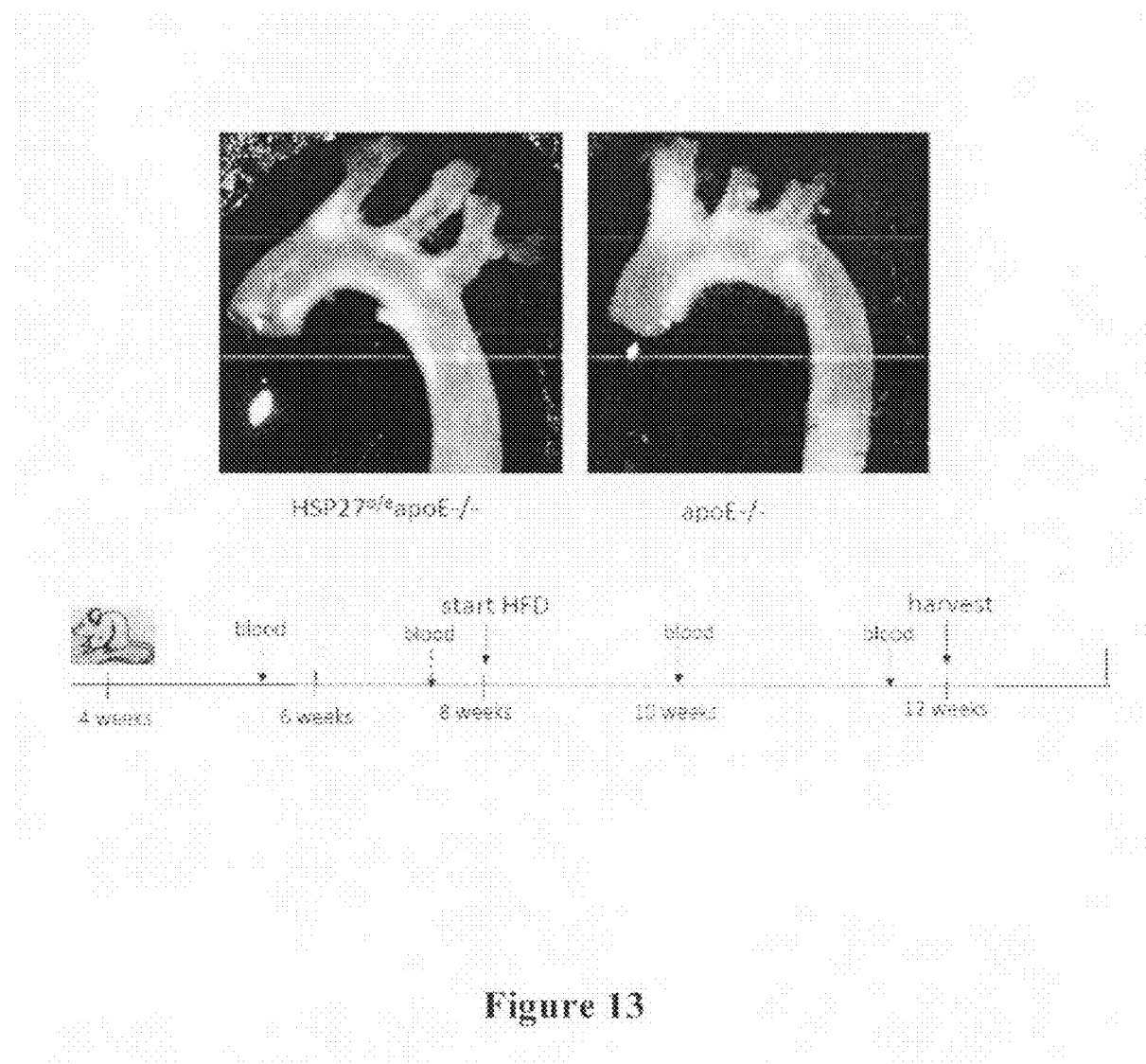
FIG. 13 shows images of dissected mice aortas and a timeline of diet and blood collection.

In FIG. 13, HSP27 over-expressing mice (HSP27o/eapoE−/−) or non-overexpressing mice (apoE−/−) were ovariectomized at 6 weeks of age and 2 weeks later placed on high fat diet. Mice were sacrificed at 12 weeks of age. Aortas were dissected and reveal no difference in lesion area in HSP27 over-expressing versus non-overexpressing mice. This appears to support previous data showing a 35% reduction in lesion area in female mice with the presence of endogenous estrogen (i.e., with the ovaries intact). These results suggest that HSP27-mediated atheroprotection requires endogenous estrogen in vivo.

Figure 14:
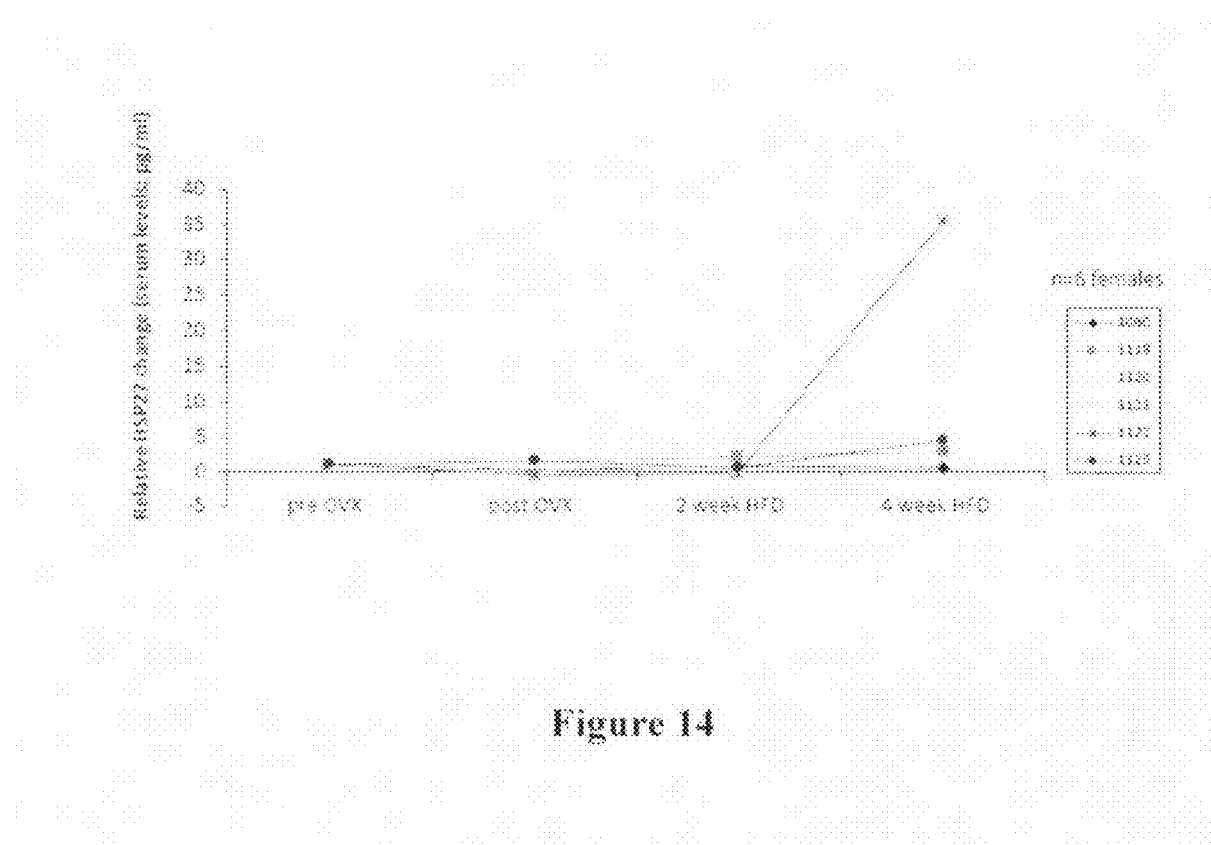
FIG. 14 shows relative HSP27 change in ovariectomized HSP27 over-expressing and non-over-expressing mice after high fat diet.

FIG. 14 shows that HSP27 serum levels remain low in ovariectomized mice. Serum was collected from HSP27 over-expressing mice (HSP27o/eapoE−/−) or non-over-expressing mice (apoE−/−) that were ovariectomized at 6 weeks of age and 2 weeks later placed on high fat diet. HSP27 ELISA analysis of the serum samples demonstrated that with the exception of 1 mouse (#1125) mice showed virtually no change in their serum HSP27 levels, indicating that high levels of release of this protein appear to be estrogen dependent.

Example 8

Gender-Related Protective Effects of HSP27 in Atherosclerosis

Figure 15:
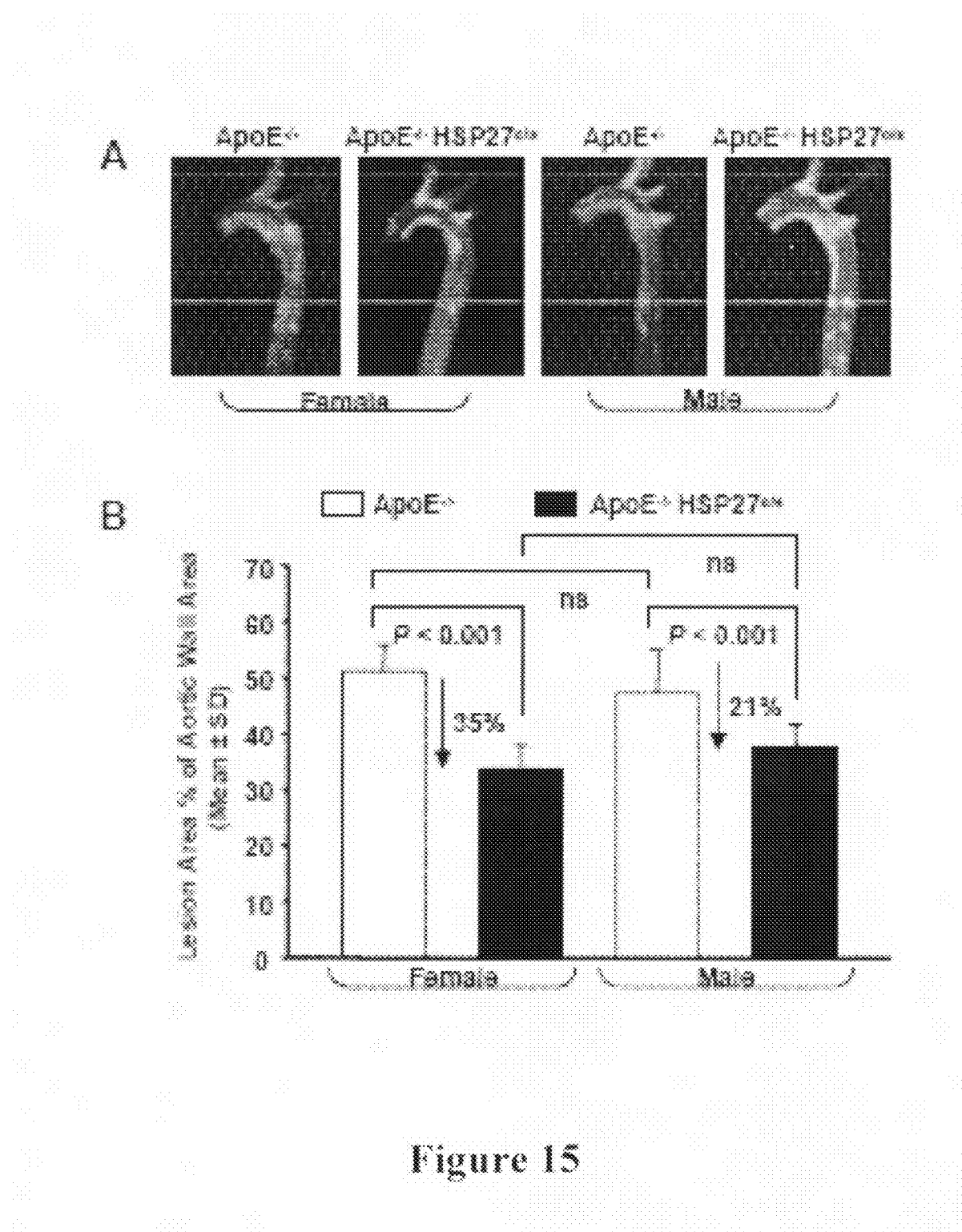
FIG. 15 shows whole aortas from HSP27 over-expression apoE−/− mice, and the quantification of aortic en face lesions.
Figure 16:
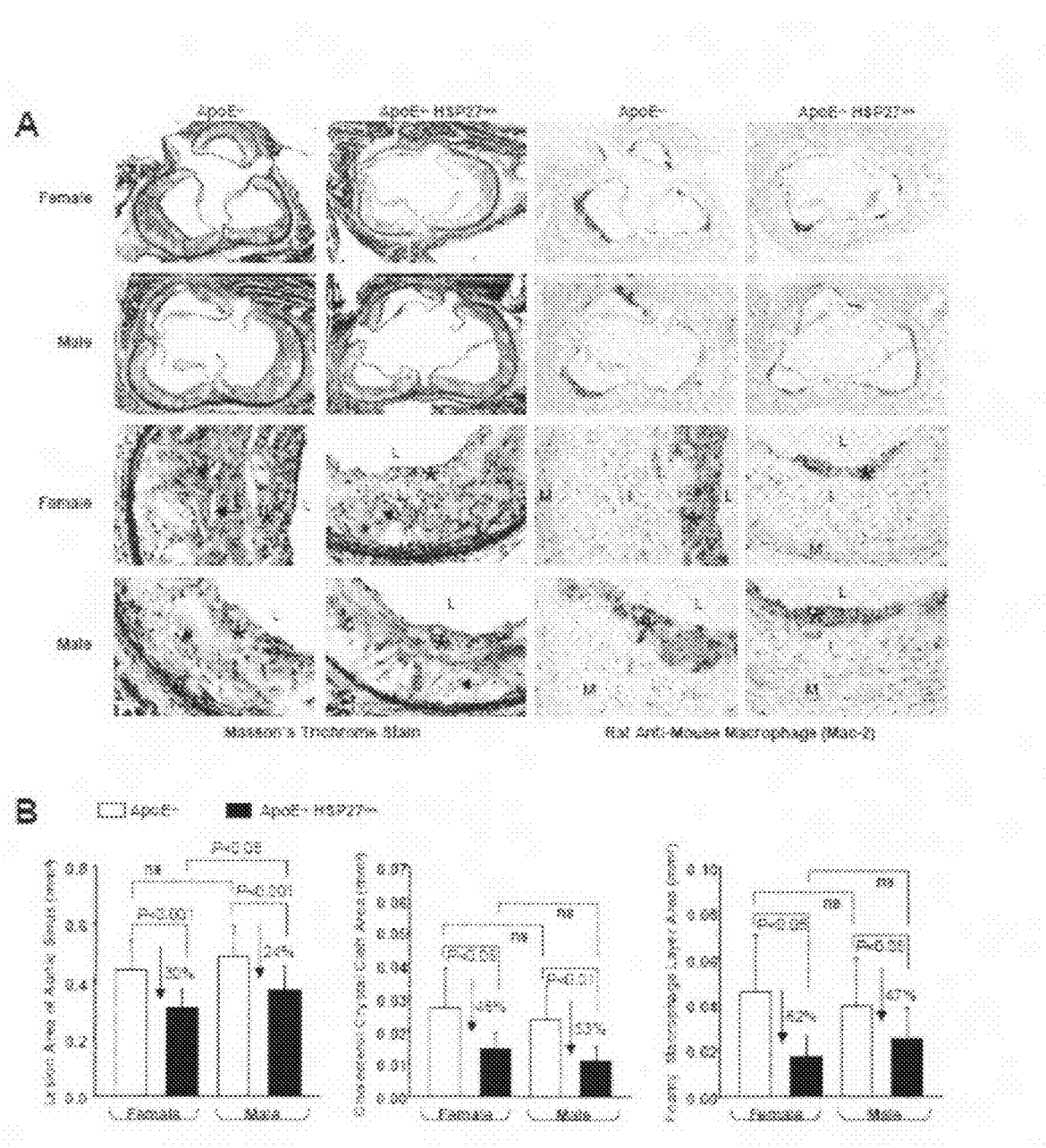
FIG. 16A shows sections from the aortic sinus of HSP27 over-expressing and non-overexpressing apoE−/− mice, and FIG. 16B aortic sinus lesion area, cholesterol cleft area and foam cell area.

FIG. 15(A) shows whole aortas from HSP27 over-expressing apoE−/−mice or non-overexpressing apoE−/− littermates after long term (12 week) atherogenic diet. FIG. 16(B) shows a quantification of aortic en face lesions expressed as lesion area as a % of total aortic area.

In FIG. 16(A), the aortic sinus of HSP27 over-expressing apoE−/−mice and non-overexpressing apoE−/− littermates was sectioned and stained for Masson's trichromestain (first 2 columns) and anti-Mac1 (last 2 columns) which labels macrophages, after long term (12 weeks) atherogenic diet. FIG. 16(B) shows aortic sinus lesion area (first graph) cholesterol cleft area (second graph) and foam cell area (third graph) quantification. This appears to suggest that HSP27 over-expression reduces foam cell formation and cholesterol cleft content in atherosclerotic lesions.

Figure 17:
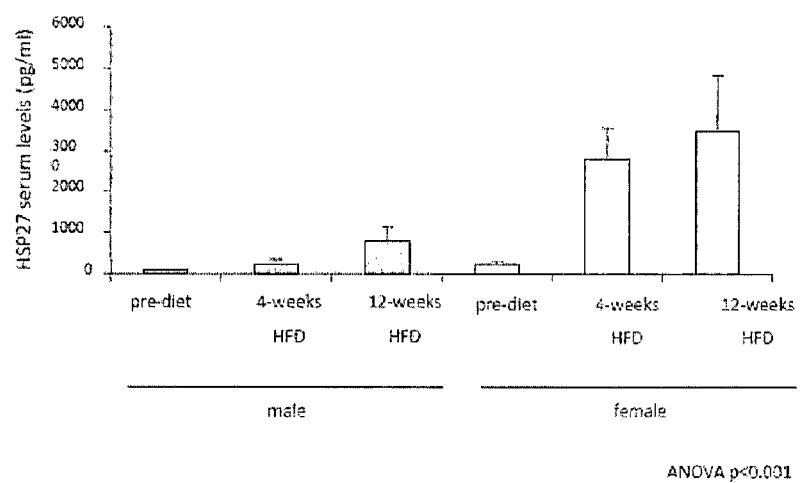
FIG. 17 shows HSP27 serum levels in male and females.

FIG. 17 shows HSP27 serum levels measured using an ELISA kit before atherogenic diet, 4 weeks post-atherogenic diet and 12 weeks post-atherogenic diet. The results show that HSP27 serum levels increase with the duration of atherogenic diet in males and females.

Example 9

Effect of Chronic Over-Expression of Heat Shock Protein 27 Reduces the Foam Cell Content of Atherosclerotic Lesions in Both Male and Female ApoE$^{-/-}$ Mice The goals of this study were i) to explore if chronic over-expression of HSP27 can provide persistent atheroprotection in females; and ii) if male mice can ultimately benefit from the effects of HSP27 on foam cell formation.

Materials and methods: For a detailed account of the Materials and Methods used in this study, please see the Supplemental Materials available online at http://circres.ahajournals.org Reduction in Atherosclerotic Lesion Area in HSP27 Over-expressing Mice: Male and female HSP27 over-expressing mice crossed to an apoE$^{-/-}$ background (apoE$^{-/-}$HSP27$^{o/e}$) and non-overexpressing apoE$^{-/-}$ littermates (apoE$^{-/-}$) were placed on a high-fat diet for 12 weeks. Female apoE$^{-/-}$HSP27$^{o/e}$ mice had a 35% reduction in aortic en face lesion area compared to apoE$^{-/-}$ females ($p \leq 0.05$; FIG. 15B). Aortic sinus lesion area was also reduced by 30% in these female apoE$^{-/-}$HSP27$^{o/e}$ mice ($p \leq 0.05$; FIG. 16B). Male apoE$^{-/-}$HSP27$^{o/e}$ had a 21% reduction in en face aortic lesion area ($p \leq 0.05$; FIG. 15B) and a 24% reduction in aortic sinus lesion area compared to their apoE$^{-/-}$ counterparts ($p \leq 0.05$; FIG. 16B). These results demonstrate that after long-term fat feeding, HSP27 maintains persistent atheroprotection in female mice, and offers a delayed but significant degree of protection in male mice.

HSP27 Over-expression and Foam Cell Content: The content of the atherosclerotic lesions in both apoE$^{-/-}$HSP27$^{o/e}$ and apoE$^{-/-}$ mice was examined by histopathology. Macrophages were stained with anti-mac2 antibodies (FIG. 16A) and foam cell content was determined as a percentage of total lesion area. Female apoE$^{-/-}$ HSP27$^{o/e}$ had a 62% decrease in foam cell content within the lesions compared to apoE−/− females ($p \leq 0.05$; FIG. 16B). Male apoE$^{-/-}$HSP27$^{o/e}$ mice had a 47% decrease in foam cell area compared to apoE$^{-/-}$ males ($p \leq 0.05$; FIG. 16B). These data demonstrate that HSP27 is capable of reducing foam cell incorporation into atherosclerotic lesion areas in both male and female mice.

Serum HSP27 Levels in Male and Female Mice: Serum levels of HSP27 were assessed in all mice before the commencement of high fat diet, as well as following 12 weeks of high fat diet. Prior to fat feeding, both male and female mice had relatively low levels of HSP27 in the serum (74±23 pg/ml and 211±116 pg/ml, respectively). Following 12 weeks of high-fat diet, serum levels of HSP27 in female mice were dramatically increased (−3473±1340 pg/ml) and males had a more modest increase in serum HSP27 (806±351 pg/ml) (FIG. 17). This appears to indicate that not only does estrogen increase HSP27 release into the serum, but atherogenic stimuli also seem to cause HSP27 to be secreted over time.

In the current study, after 12 weeks of high-fat feeding, HSP27 over-expression was capable of maintaining its protective effects in female mice, with a reduction in overall lesion area as well as foam cell content. However, unlike what was observed previously in the 4-week study [43], after 12 weeks of high fat diet male mice were afforded a 20-25% reduction in overall lesion area, and a 48% reduction in foam cell content in these lesions. These results appear to suggest that HSP27 over-expression is dependent upon estrogens in the early stages of lesion development, possibly through its increased secretion in response to estrogen. However, at more advanced stages of lesion development, HSP27 seems to cause an overall reduction in foam cell content in both males and females, possibly through its effects in macrophage migration, adhesion, and atherogenic lipid uptake. HSP27 levels in the serum peak very early in female mice, with 15-fold higher levels observed in females compared to males after 4 weeks. However, after 12 weeks of high-fat feeding, male HSP27 serum levels begin to increase, possibly in response to atherogenic lipids—an effect that was previously observed in vitro. Serum levels of HSP27 in the female mice however remain high, but do not increase relative to their levels after 4 weeks. This suggests that HSP27 in the serum peaks early in female mice, potentially offering a protective effect early in lesion development. In male mice (i.e. in the absence of estrogen) atherogenic lipids cause a slower release of HSP27, taking longer to exert their beneficial effects.

It had previously noted that macrophages from apoE$^{-/-}$HSP27$^{o/e}$ mice show both reduced migration and adhesion compared to apoE$^{-/-}$ macrophages. This may be another mechanism by which HSP27 is exerting its protective effects, and why reduced foam cell content in both male and female over-expressing mice is seen.

Taken together, these data appear to suggest that HSP27 is atheroprotective in both sexes, possibly offering its beneficial effects earlier in lesion development in female mice. In males, possibly due to lack of estrogen, HSP27 provides atheroprotection later in lesion development. Both male and female HSP27 over-expressing mice had reduced foam cell content in their lesions compared to their non-overexpressing littermates, confirming the role for HSP27 in the reduction in foam cell formation.

Example 10

Response to Injury

Figure 18:
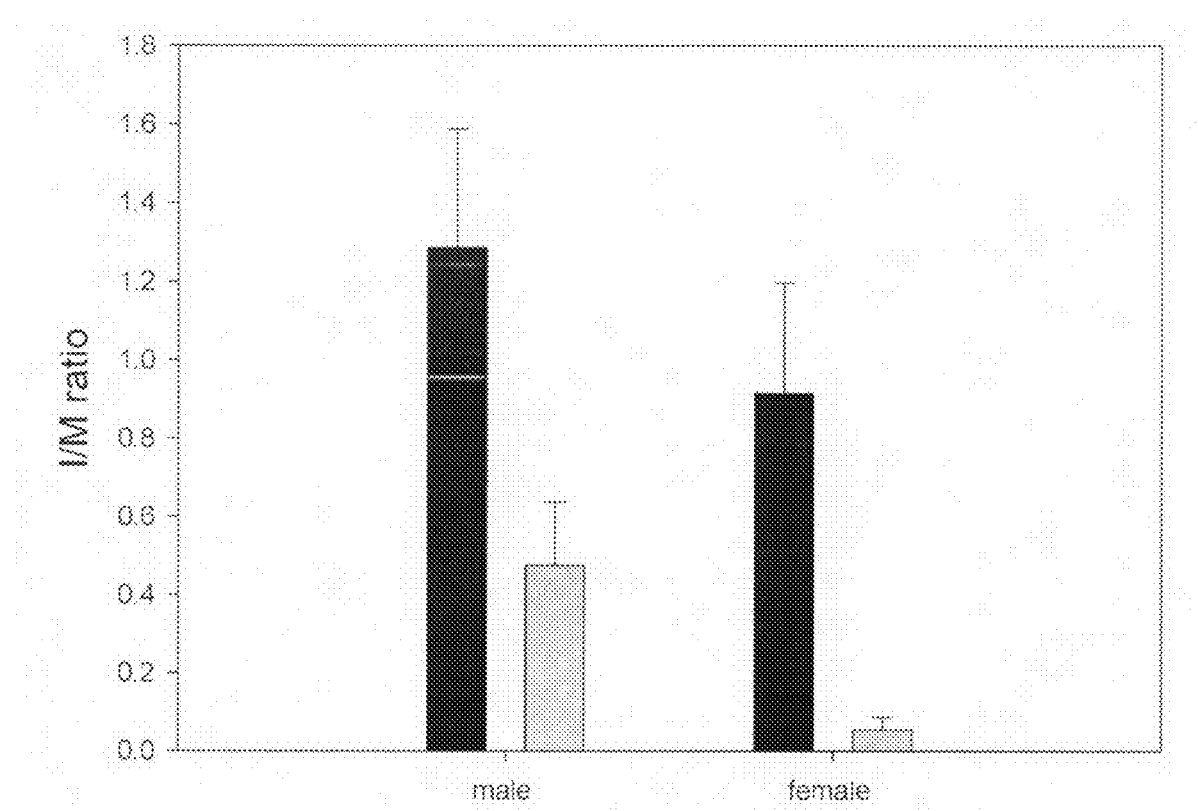
FIG. 18 shows intima to media ratio (I/M ratio) in HSP27 over-expressing (HSP27o/e) and non-overexpressing (WT) mice subjected to femoral artery wire injury.

As illustrated in FIG. 18, HSP27 over-expressing (HSP27o/e) and non-overexpressing (WT) mice were subjected to femoral artery wire injury. The arteries were harvested 28 days post-injury, and the intima to media ratio (I/M ratio) was determined. HSP27 over-expression results in a decrease in neo-intima formation in both male and female mice, with a more dramatic effect observed in females.

SUMMARY

As disclosed herein, there is a reduction in circulating levels of HSP27 in the serum of individuals suffering from coronary artery disease compared to healthy controls. This data agrees with that reported for patients with carotid stenosis >50%, who had a 20-fold decrease in circulating HSP27 levels compared to healthy individuals[13]. Moreover, the reduction in circulating HSP27 is reversed when patients are suffering from an acute coronary event, implying that HSP27 may be secreted into the extracellular space in response to cardiac ischemia. Previous reports in ACS patients demonstrate that within 24 hours of an acute event, HSP27 levels are increased approximately 2-fold compared to reference subjects[14]. Surprisingly, patients who have stable disease have significantly lower levels of HSP27 in the blood, which may indicate that this protein offers some long-term protection from the development of atherosclerosis. It has been established that HSP27 expression in the vessel wall is lost as atherosclerosis progresses; thus, high levels of HSP27 in both the vasculature and circulation is likely atheroprotective.

Transgenic mice studies indicate the possible in vivo ability of HSP27 to protect against the development of atherosclerosis. When transgenic mice over-expressing human HSP27 were crossed with atherosclerosis-prone apoE-null mice, the female HSP27 over-expressing mice had a 41% reduction in atherosclerotic lesion area—an effect that was absent in males. As previously shown, HSP27 is an estrogen receptor beta (ERβ) associated protein that is capable of modulating estrogen signaling via transcriptional repression of the receptor. The current observation that the protective effects of HSP27 may be sex-specific highlight the overall importance of this protein in estrogen biology. It also noted that HSP27 in the serum is significantly higher in these same female mice compared to their male littermates, indicating that the circulating HSP27 is likely offering some protection against the development of disease, and these levels in male mice are likely not sufficiently elevated to achieve this protective effect. The degree of correlation between circulating HSP27 levels and total aortic lesion area is noteworthy, showing a correlation coefficient of 0.90. This appears to indicate that HSP27 levels in humans may be highly predictive of atherosclerotic lesion burden.

HSP27 over-expression has been shown to be protective against a variety of stressful and/or pathogenic stimuli (e.g. ischemia/reperfusion injury, gastromucosal injury, nerve injury)[17, 24-27], but these are the first observations to date that this protection may be sex-specific. The mechanism of release of HSP27 into the serum and how ovarian hormones are affecting this process may be indicative of the enhancement of the overall protective effects of HSP27.

In vivo data of how HSP27 exits the cell and enters the serum (i.e., extracellular space) show that HSP27 is only detectable in the serum following a high-fat/atherogenic diet, in both males and females. Corresponding in vitro studies showed that by treating macrophages with high levels of acLDL and demonstrate that indeed HSP27 appears to be released into the extracellular space under these conditions. As known in the art, oxidized LDL is capable of inducing HSP70 secretion from macrophages[28]. Given that HSP27 is primarily described as an intracellular protein, the mechanism by which HSP27 may exit the cell has never been described. The fact that HSP27 does not contain signal sequences or peptides that would sort it to a traditional secretory vesicle renders the mechanism of HSP27 to be surprising. On examining the lysosomal pathway, it was noted that in mouse macrophages treated with high levels of acLDL, HSP27 was seen in secretory-like granules, and co-localizes with the lysosome. Others have described the same mechanism for the secretion of other heat shock proteins, namely HSP70[29]. This mechanism for heat shock secretion is also very similar to that described for interleukin-1, an important inflammatory stimulus[30]. The idea that HSP27 is secreted in response to atherogenic stimuli, and that higher levels of HSP27 correlate with lower disease burden in both mice and humans suggests that extracellular HSP27 is perhaps an novel protector of atherosclerotic disease and hence an attractive target for future therapeutics. HSP27, as a member of the heat shock protein family, may also be a therapeutic target in diseases other than cardiovascular disease, such as cancer, diabetes, and the like. In particular, HSP27 may be a potential therapeutic target in gender-specific diseases, such as ovarian or prostate cancer, either in prophylaxis or treatment thereof. It may also serve as a diagnostic biomarker for these and other gender- or age-dependent diseases.

A novel and important aspect of the present invention is the interaction of HSP27 and the scavenger receptor A. Not only is this interaction specific, as demonstrated using a competitor for SR-A as well as SR-A-null macrophages, but HSP27 appears to reduce the ability of SR-A on the surface of macrophages to engulf acLDL and acquire the foam cell phenotype. This is the first known evidence of a cell-surface receptor for HSP27. Previous reports show that the heat shock protein family is capable of binding a variety of receptors, namely those involved in antigen recognition and immune signaling (reviewed by[31]. For example, HSP70 has been shown to bind to and signal through the toll-like receptors 2 and 4 (TLR-2 and -4), inducing NFκB activation and IL-6 production[18]. Other reports show that SR-A is capable of binding Gp96 an endoplasmic-reticulum bound HSP, on antigen presenting cells[32]. Moreover, many studies conclude that extracellular HSPs are primarily pro-inflammatory stimuli. Recombinant HSP70 secreted from macrophages in vitro induced the secretion of IL-1β, and IL-12, both pro-inflammatory cytokines.

Surprisingly, HSP27 has been shown in the present invention to have opposite effects. When added to macrophages in vitro, HSP27 reduced the acLDL-induced secretion of IL-1β, and increased the secretion of IL-10, which imply that HSP27 primarily results in anti-inflammatory cytokine induction. Relative to peritoneal macrophages from apoE$^{-/-}$ mice, apoE$^{-/-}$HSP27$^{o/e}$ macrophages showed decreased cell adhesion and migration—two additional mechanisms by which vessel wall inflammation may have been reduced in vivo with over-expression of HSP27. Taken together, these data suggest a novel mechanism by which extracellular HSP27 is capable of preventing the uptake of atherogenic lipids and reducing inflammation associated with this uptake, therefore perhaps reducing overall atherosclerotic burden. Compounds which interact with the SR-A receptor may also be contemplated in the context of the present invention, working either agonistically or antagonistically.

To further explore the mechanism by which HSP27 over-expression may reduce the progression in a mouse-model of atherosclerosis, peritoneal macrophages were harvested from HSP27$^{o/e}$apoE–/– and WT apoE–/– to test the characteristics of these cells in vitro. HSP27 over-expression resulted in a significant decrease in both cell adhesion and migration, indicating that these cells in vivo may have decreased incorporation into atherosclerotic plaques. Combined with the observation that HSP27 can reduce atherogenic lipid uptake and inflammatory cytokine release, it appears that the mechanism of atheroprotection of HSP27 involves virtually all hallmark processes involved in disease progression.

In the current invention, there is provided a likely novel mechanism of HSP27 protection that involves HSP27 as an extracellular signal capable of modulating the response to atherogenic stimuli. HSP27 appears to have the potential of preventing macrophage incorporation into the developing plaque, and subsequent ability not only to reduce foam cell formation, but also the inflammation that accompanies this process. Clearly, the implications of this novel role for HSP27 are likely far-reaching, uncovering the possibility for HSP27 to become a new target for cholesterol-altering and anti-inflammatory therapeutics.

Other factors may be involved which contribute to the role of HSP27 in modulating atherosclerosis. Studies, such as microarray analysis and the like, may reveal that certain genes have similar expression profiles of HSP27 in various states of cardiovascular disease, such as atherosclerosis. HSP27 copy number using RT-PCR may be determined. These studies may also reveal additional targets or co-factors which may help ameliorate the effects of HSP27 on preventing and/or treating atherosclerosis, or other diseases in a subject requiring prevention or treatment thereof. Other targets and co-factors may also be contemplated in the context of the present invention.

Hydroxy-methylglutaryl-coenzyme A reductase is the rate limiting enzyme in the synthesis of cholesterol. Currently, the most popular class of cholesterol lowering medications is characterized by the common inhibition of 3-hydroxy-3-methylglutaryl Coenzyme A reductase, and because of the common terminal syllables used to name these drugs, they are often referred to as "statins". Treatment of patients with a "statin" is associated with altered HSP27 extracellular levels.

HSP27 may also be an important extracellular chaperone capable of binding key de-natured proteins and protecting the vessel wall from insult/injury. The binding of HSP27 to serum derived proteins from patients with and without coronary artery disease may be analyzed and quantified, particularly in real time. This may be achieved with any known methods in the art, such as immobilizing the HSP27 protein on a chip and using surface plasmon resonance technology (Biacore Inc).

The above-described embodiments of the present invention are intended to be examples only. Alterations, modifications and variations may be effected to the particular embodiments by those of skill in the art without departing from the scope of the invention, which is defined solely by the claims appended hereto.

REFERENCE LIST (1) Miller H, Poon S, Hibbert B, Rayner K, Chen Y-X, O'Brien E R. Modulation of estrogen signaling by the novel interaction of heat shock protein 27, a biomarker for atherosclerosis, and estrogen receptor β. *Arterioscler Thromb Vasc Biol* 2005; 25:e10-e14.

(2) Hulley S, Grady D, Bush T et al. Randomized Trial of Estrogen Plus Progestin for Secondary Prevention of Coronary Heart Disease in Postmenopausal Women. *JAMA: The Journal of the American Medical Association* 1998 Aug. 19; 280(7):605-13.

(3) Writing Group for the Women's Health Initiative Investigators. Risks and Benefits of Estrogen Plus Progestin in Healthy Postmenopausal Women: Principal Results From the Women's Health Initiative Randomized Controlled Trial. *JAMA: The Journal of the American Medical Association* 2002 Jul. 17; 288(3):321-33.

(4) Waters D D, Gordon D, Rossouw J E et al. Women's Ischemic Syndrome Evaluation: Current Status and Future Research Directions Report of the National Heart, Lung and Blood Institute Workshop: Oct. 2-4, 2002: Section 4: Lessons From Hormone Replacement Trials. *Circulation* 2004 Feb. 17; 109(6):53e-55.

(5) Turgeon J L, McDonnell D P, Martin K A, Wise P M. Hormone Therapy: Physiological Complexity Belies Therapeutic Simplicity. *Science* 2004 May 28; 304(5675): 1269-73.

(6) Mendelsohn M E, Karas R H. The time has come to stop letting the HERS tale wag the dogma. *Circulation* 2001 Nov. 6; 104(19):2256-9.

(7) Losel R M, Falkenstein E, Feuring M et al. Nongenomic Steroid Action: Controversies, Questions, and Answers. *Physiol Rev* 2003 Jul. 1; 83(3):965-1016.

(8) Hall J M, Couse J F, Korach K S. The Multifaceted Mechanisms of Estradiol and Estrogen Receptor Signaling. *Journal of Biological Chemistry* 2001 Sep. 28; 276 (40):36869-72.

(9) Mendelsohn M E, Karas R H. The protective effects of estrogen on the cardiovascular system. *N Eng J Med* 1999; 340(23):1801-11.

(10) Smith C L, O'Malley B W. Coregulator Function: A Key to Understanding Tissue Specificity of Selective Receptor Modulators. *Endocr Rev* 2004; 25(1):45-71.

(11) Lindner V, Kim S K, Karas R H, Kuiper G J M, Gustafsson J-A, Mendelsohn M E. Increased expression of estrogen receptor-beta mRNA in male blood vessels after vascular injury. *Circ Res* 1998; 83:224-9.

(12) Makela S, Savolainen H, Aavik E et al. Differentiation between vasculoprotective and uterotrophic effects of ligands with different binding affinities to estrogen receptors alpha and beta. *Proc Natl Acad Sci USA* 1999; 96(12): 7077-82.

(13) Martin-Ventura J L, Duran M C, Blanco-Colio L M et al. Identification by a differential proteomic approach of heat shock protein 27 as a potential marker of atherosclerosis. *Circulation* 2004; 110:2216-9.

(14) Park H K, Park E C, Bae S W et al. Expression of heat shock protein 27 in human atherosclerotic plaques and increased plasma level of heat shock protein 27 in patients with acute coronary syndrome. *Circulation* 2006 Aug. 29; 114(9):886-93.

(15) Wagstaff M J, Collaco-Moraes Y, Smith J, de Belleroche J S, Coffin R S, Latchman D S. Protection of neuronal cells from apoptosis by Hsp27 delivered with a herpes simplex virus-based vector. *J Biol Chem* 1999 Feb. 19; 274(8): 5061-9.

(16) Concannon C G, Gorman A M, Samali A. On the role of Hsp27 in regulating apoptosis. *Apoptosis* 2003 January; 8(1):61-70.

(17) Zourlidou A, Gidalevitz T, Kristiansen M et al. Hsp27 overexpression in the R6/2 mouse model of Huntington's disease: chronic neurodegeneration does not induce Hsp27 activation. *Hum Mol Genet* 2007 May 1; 16(9):1078-90.

(18) Asea A, Rehli M, Kabingu E et al. Novel signal transduction pathway utilized by extracellular HSP70: role of toll-like receptor (TLR) 2 and TLR4. *J Biol Chem* 2002 Apr. 26; 277(17):15028-34.

(19) Vabulas R M, hmad-Nejad P, Ghose S, Kirschning C J, Issels R D, Wagner H. HSP70 as endogenous stimulus of the Toll/interleukin-1 receptor signal pathway. *J Biol Chem* 2002 Apr. 26; 277(17):15107-12.

(20) Vabulas R M, Braedel S, Hilf N et al. The endoplasmic reticulum-resident heat shock protein Gp96 activates dendritic cells via the Toll-like receptor 2/4 pathway. *J Biol Chem* 2002 Jun. 7; 277(23):20847-53.

(21) Vabulas R M, hmad-Nejad P, Da C C et al. Endocytosed HSP60s use toll-like receptor 2 (TLR2) and TLR4 to activate the toll/interleukin-1 receptor signaling pathway in innate immune cells. *J Biol Chem* 2001 Aug. 17; 276(33): 31332-9.

(22) Moore K J, Freeman M W. Scavenger receptors in atherosclerosis: beyond lipid uptake. *Arterioscler Thromb Vasc Biol* 2006 August; 26(8):1702-11.

(23) Kunjathoor U V, Febbraio M, Podrez E A et al. Scavenger receptors class A-I/II and CD36 are the principal receptors responsible for the uptake of modified low density lipoprotein leading to lipid loading in macrophages. *J Biol Chem* 2002 Dec. 20; 277(51):49982-8.

(24) Sharp P, Krishnan M, Pullar O, Navarrete R, Wells D, de B J. Heat shock protein 27 rescues motor neurons following nerve injury and preserves muscle function. *Exp Neurol* 2006 April; 198(2):511-8.

(25) Hollander J M, Martin J L, Belke D D et al. Overexpression of wild-type heat shock protein 27 and a nonphosphorylatable heat shock protein 27 mutant protects against ischemia/reperfusion injury in a transgenic mouse model. *Circulation* 2004; 110:3544-52.

(26) Liu L, Zhang X, Qian B et al. Over-expression of heat shock protein 27 attenuates doxorubicin-induced cardiac dysfunction in mice. *Eur J Heart Fail* 2007 May 2.

(27) Akbar M T, Lundberg A M C, Liu K et al. The Neuroprotective Effects of Heat Shock Protein 27 Overexpression in Transgenic Animals against Kainate-induced Seizures and Hippocampal Cell Death. *Journal of Biological Chemistry* 2003 May 23; 278(22):19956-65.

(28) Svensson P A, Asea A, Englund M C et al. Major role of HSP70 as a paracrine inducer of cytokine production in human oxidized LDL treated macrophages. *Atherosclerosis* 2006 March; 185(1):32-8.

(29) Mambula S S, Calderwood S K. Heat shock protein 70 is secreted from tumor cells by a nonclassical pathway involving lysosomal endosomes. *J Immunol* 2006 Dec. 1; 177(11):7849-57.

(30) Andrei C, Margiocco P, Poggi A, Lotti L V, Torrisi M R, Rubartelli A. Phospholipases C and A2 control lysosome-mediated IL-1 beta secretion: Implications for inflammatory processes. *Proc Nat Acad Sci USA* 2004 Jun. 29; 101 (26):9745-50.

(31) Binder R J, Vatner R, Srivastava P. The heat-shock protein receptors: some answers and more questions. *Tissue Antigens* 2004 October; 64(4):442-51.

(32) Berwin B, Hart J P, Rice S et al. Scavenger receptor-A mediates gp96/GRP94 and calreticulin internalization by antigen-presenting cells. *EMBO J.* 2003 Nov. 17; 22(22): 6127-36.

(33) Redon R, Ishikawa S, Fitch K R et al. Global variation in copy number in the human genome. *Nature* 2006 Nov. 23; 444(7118):444-54.

(34) Stranger B E, Forrest M S, Dunning M et al. Relative impact of nucleotide and copy number variation on gene expression phenotypes. *Science* 2007 Feb. 9; 315(5813): 848-53.

(35) Wang J, Ban M R, Hegele R A. Multiplex ligation-dependent probe amplification of LDLR enhances molecular diagnosis of familial hypercholesterolemia. *J Lipid Res* 2005 February; 46(2):366-72.

(36) Feuk L, Carson A R, Scherer S W. Structural variation in the human genome. *Nat Rev Genet.* 2006 February; 7(2): 85-97.

(37) Hegele R A. Copy-number variations add a new layer of complexity in the human genome. *CMAJ* 2007 Feb. 13; 176(4):441-2.

(38) Redon R, Ishikawa S, Fitch K R et al. Global variation in copy number in the human genome. *Nature* 2006 Nov. 23; 444(7118):444-54.

(39) Freeman J L, Perry G H, Feuk L et al. Copy number variation: new insights in genome diversity. *Genome Res* 2006 August; 16(8):949-61.

(40) Feuk L, Marshall C R, Wintle R F, Scherer S W. Structural variants: changing the landscape of chromosomes and design of disease studies. *Hum Mol Genet.* 2006 Apr. 15; 15 Spec No 1:R57-R66.

(41) Redon R, Ishikawa S, Fitch K R et al. Global variation in copy number in the human genome. *Nature* 2006 Nov. 23; 444(7118):444-54.

(42) Chen Q, Book M, Fang X, Hoeft A, Stuber F. Screening of copy number polymorphisms in human beta-defensin genes using modified real-time quantitative PCR. *J Immunol Methods* 2006 Jan. 20; 308(1-2):231-40.

(43) Rayner K, Chen Y X, McNulty M, Simard T, Zhao X, Wells D J, de Belleroche J., O'Brien E R. Extracellular Release of the Atheroprotective Heat Shock Protein 27 Is Mediated by Estrogen and Competitively Inhibits acLDL Binding to Scavenger Receptor-A. *Circ Res* 2008 Jun. 19; 103:133-41.

What is claimed is:

1. A method for treating cardiovascular disease in a human subject with atherosclerosis, comprising:
   administering to said subject a therapeutically effective amount of heat shock protein 27 or a functional variant of heat shock protein 27 to maintain a serum level of heat shock protein 27 or the functional variant of heat shock protein 27, of at least 828 pg/mL.

2. The method of claim 1, wherein the cardiovascular disease to be treated is atherosclerosis.

3. The method of claim 2, wherein the cardiovascular disease to be treated is coronary atherosclerosis.

4. The method of claim 1, wherein the subject is female.

5. The method of claim 1, wherein the subject has coronary artery disease.

6. A method for treating cardiovascular disease in a human subject with atherosclerosis, comprising:
   administering to said subject a therapeutically effective amount of heat shock protein 27 or a functional variant of heat shock protein 27 to increase the serum level of heat shock protein 27 or the functional variant of heat shock protein 27, to at least 828 pg/mL.

7. The method of claim 6, wherein the cardiovascular disease to be treated is atherosclerosis.

8. The method of claim 6, wherein the cardiovascular disease to be treated is coronary atherosclerosis.

9. The method of claim 6, wherein the subject is female.

10. The method of claim 6, wherein the subject has coronary artery disease.

* * * * *